US009427142B2

(12) United States Patent
Terliuc

(10) Patent No.: US 9,427,142 B2
(45) Date of Patent: Aug. 30, 2016

(54) BALLOON GUIDED ENDOSCOPY

(75) Inventor: Gad Terliuc, Ra'anana (IL)

(73) Assignee: Smart Medical Systems Ltd, Ra'anana (IL)

( * ) Notice: Subject to any disclaimer, the term of this patent is extended or adjusted under 35 U.S.C. 154(b) by 857 days.

(21) Appl. No.: 11/990,194

(22) PCT Filed: Aug. 8, 2005

(86) PCT No.: PCT/IL2005/000849
§ 371 (c)(1),
(2), (4) Date: Feb. 6, 2008

(87) PCT Pub. No.: WO2007/017854
PCT Pub. Date: Feb. 15, 2007

(65) Prior Publication Data
US 2009/0227835 A1   Sep. 10, 2009

(51) Int. Cl.
| A61B 1/00 | (2006.01) |
| A61B 1/31 | (2006.01) |
| A61B 1/005 | (2006.01) |
| A61B 1/018 | (2006.01) |

(52) U.S. Cl.
CPC .............. *A61B 1/31* (2013.01); *A61B 1/005* (2013.01); *A61B 1/00082* (2013.01); *A61B 1/018* (2013.01)

(58) Field of Classification Search
USPC ............. 600/114–116, 153, 156, 158, 128, 600/139–140, 143–144, 146; 604/96.01, 604/101.02, 101.04, 102.02, 103.03
See application file for complete search history.

(56) References Cited

U.S. PATENT DOCUMENTS

| 3,913,565 | A | * | 10/1975 | Kawahara ............... 600/585 |
| 4,040,413 | A |   | 8/1977  | Ohshiro |
| 4,066,070 | A |   | 1/1978  | Utsugi |
| 4,148,307 | A |   | 4/1979  | Utsugi |
| 4,176,662 | A |   | 12/1979 | Frazer |
| 4,195,633 | A |   | 4/1980  | Nehring et al. |
| 4,195,637 | A |   | 4/1980  | Gruntzig et al. |
| 4,224,929 | A |   | 9/1980  | Furihata |
| 4,231,365 | A | * | 11/1980 | Scarberry ............... 128/207.15 |
| 4,445,892 | A | * | 5/1984  | Hussein et al. ......... 604/101.05 |
| 4,453,545 | A |   | 6/1984  | Inoue |
| 4,584,998 | A | * | 4/1986  | McGrail ............... 128/207.15 |
| 4,616,631 | A | * | 10/1986 | Takahashi ............... 600/139 |
| 4,616,652 | A |   | 10/1986 | Simpson |
| 4,646,722 | A |   | 3/1987  | Silverstein et al. |
| 4,646,988 | A |   | 3/1987  | Campbell |
| 4,676,228 | A |   | 6/1987  | Krasner et al. |
| 4,807,593 | A |   | 2/1989  | Ito |

(Continued)

FOREIGN PATENT DOCUMENTS

| WO | WO 83/01893 | 6/1983 |
| WO | WO 99/53827 | 10/1999 |

(Continued)

OTHER PUBLICATIONS

An English Abstract of JP 2003-250896, Sep. 2003.

(Continued)

*Primary Examiner* — Matthew J Kasztejna
(74) *Attorney, Agent, or Firm* — Abelman, Frayne & Schwab

(57) ABSTRACT

An endoscope assembly including an endoscope, a selectably inflatable balloon mounted onto a distal portion of the endoscope and an external tube extending alongside the endoscope and traversing the selectably inflatable balloon.

15 Claims, 29 Drawing Sheets

(56) References Cited

U.S. PATENT DOCUMENTS

| | | | |
|---|---|---|---|
| 4,862,874 A * | 9/1989 | Kellner | 600/116 |
| 4,983,165 A | 1/1991 | Loiterman | |
| 5,025,778 A | 6/1991 | Silverstein et al. | |
| 5,050,585 A | 9/1991 | Takahashi | |
| 5,135,001 A | 8/1992 | Sinofsky et al. | |
| 5,259,366 A | 11/1993 | Reydel et al. | |
| 5,263,928 A * | 11/1993 | Trauthen et al. | 604/509 |
| 5,411,016 A * | 5/1995 | Kume | A61B 1/00082 600/114 |
| 5,483,951 A * | 1/1996 | Frassica et al. | 600/104 |
| 5,507,726 A * | 4/1996 | Johnson et al. | 604/102.02 |
| 5,518,501 A | 5/1996 | Oneda et al. | |
| 5,549,553 A * | 8/1996 | Ressemann et al. | 604/103.08 |
| 5,577,992 A | 11/1996 | Chiba et al. | |
| 5,588,424 A * | 12/1996 | Insler et al. | 128/207.15 |
| 5,662,587 A | 9/1997 | Grundfest et al. | |
| 5,679,110 A | 10/1997 | Hamazaki | |
| 5,704,899 A * | 1/1998 | Milo | A61B 1/0056 385/107 |
| 5,718,712 A | 2/1998 | Bonnal | |
| 5,762,604 A | 6/1998 | Kieturakis | |
| 5,868,662 A * | 2/1999 | Borodulin et al. | 600/105 |
| 5,876,329 A | 3/1999 | Harhen | |
| 5,938,586 A | 8/1999 | Wilk et al. | |
| 6,007,482 A | 12/1999 | Madni et al. | |
| 6,161,049 A | 12/2000 | Rudie et al. | |
| 6,162,171 A | 12/2000 | Ng et al. | |
| 6,306,081 B1 * | 10/2001 | Ishikawa et al. | 600/127 |
| 6,309,346 B1 | 10/2001 | Farhadi | |
| 6,428,566 B1 * | 8/2002 | Holt | 600/141 |
| 6,461,294 B1 | 10/2002 | Oneda et al. | |
| 6,485,409 B1 | 11/2002 | Voloshin et al. | |
| 6,540,670 B1 * | 4/2003 | Hirata et al. | 600/152 |
| 6,585,639 B1 | 7/2003 | Kotmel et al. | |
| 6,663,589 B1 | 12/2003 | Halevy | |
| 6,702,735 B2 | 3/2004 | Kelly | |
| 6,951,554 B2 | 10/2005 | Johansen et al. | |
| 7,056,284 B2 | 6/2006 | Martone et al. | |
| 7,169,105 B2 | 1/2007 | Iwasaka et al. | |
| 7,637,905 B2 * | 12/2009 | Saadat et al. | 606/1 |
| 2002/0143237 A1 | 10/2002 | Oneda et al. | |
| 2002/0156347 A1 | 10/2002 | Kim et al. | |
| 2003/0083547 A1 * | 5/2003 | Hamilton et al. | 600/116 |
| 2003/0130564 A1 * | 7/2003 | Martone et al. | 600/121 |
| 2004/0102681 A1 | 5/2004 | Gross | |
| 2005/0038335 A1 | 2/2005 | Gross et al. | |
| 2005/0059931 A1 | 3/2005 | Garrison et al. | |
| 2005/0124856 A1 | 6/2005 | Fujikura et al. | |
| 2005/0125005 A1 | 6/2005 | Fujikura | |
| 2005/0133453 A1 | 6/2005 | Woodruff et al. | |
| 2005/0137457 A1 * | 6/2005 | Machida | 600/115 |
| 2005/0154355 A1 * | 7/2005 | Gross et al. | 604/232 |
| 2005/0159645 A1 | 7/2005 | Bertolero et al. | |
| 2005/0165233 A1 | 7/2005 | Hamedi et al. | |
| 2005/0165273 A1 | 7/2005 | Takano | |
| 2005/0273021 A1 | 12/2005 | Burgermeister | |
| 2006/0111610 A1 | 5/2006 | Machida | |
| 2006/0161044 A1 | 7/2006 | Oneda et al. | |
| 2006/0241345 A1 | 10/2006 | Oishi et al. | |
| 2007/0244361 A1 | 10/2007 | Ikeda et al. | |
| 2009/0227835 A1 | 9/2009 | Terliuc | |

FOREIGN PATENT DOCUMENTS

| | | |
|---|---|---|
| WO | WO 02/064028 | 8/2002 |
| WO | WO 03/080155 | 10/2003 |
| WO | WO 2004/101059 | 11/2004 |
| WO | 2007017854 A2 | 2/2007 |

OTHER PUBLICATIONS

An Office Action dated Sep. 28, 2009, which issued during the prosecution of Applicant's Australian Patent Application No. 2005211257.

An Office Action dated Oct. 9, 2009, which issued during the prosecution of Applicant's U.S. Appl. No. 10/588,131.

An Office Action dated Apr. 9, 2010, which issued during the prosecution of Applicant's U.S. Appl. No. 10/588,131.

An Office Action dated Nov. 3, 2007, which issued during the prosecution of Applicant's Chinese Patent Application No. 200580004311.4.

An Office Action dated Jan. 25, 2010, which issued during the prosecution of Applicant's Chinese Patent Application No. 200810173921.2.

An International Search Report dated Sep. 1, 2005, which issued during the prosecution of Applicant's PCT/IL05/00152.

An International Search Report dated Jun. 2, 2010, which issued during the prosecution of Applicant's PCT/IL09/00940.

An International Search Report dated Sep. 1, 2009, which issued during the prosecution of Applicant's PCT/IL09/00322.

An International Search Report dated Jul. 9, 2009, which issued during the prosecution of Applicant's PCT/IL08/00687.

An International Search Report dated Jul. 18, 2008, which issued during the prosecution of Applicant's PCT/IL07/00832.

An International Search Report dated Apr. 21, 2008, which issued during the prosecution of Applicant's PCT/IL05/00849.

An International Search Report dated May 19, 2008, which issued during the prosecution of Applicant's PCT/IL07/00600.

An Office Action dated Mar. 23, 2009, which issued during the prosecution of Applicant's Israel Patent Application No. 177148. (Including a translation of the relevant part).

An Office Action dated Sep. 23, 2009, which issued during the prosecution of Applicant's Israel Patent Application No. 177148. (Including a translation of the relevant part).

An English Translation Regarding Prior art issues only received in an Office Action dated Jan. 2, 2013 which issued during the prosecution of Israel Patent Application No. 188957.

An Office Action dated Jan. 15, 2015 which issued during the prosecution of Canadian Patent Application No. 2618492.

Office Action from related Canadian Patent Application No. 2618492, dated Dec. 18, 2015 (3 pages).

Office Action from related Indian Patent Application No. 1344/DELNP/2008, dated Oct. 30, 2015 (2 pages).

* cited by examiner

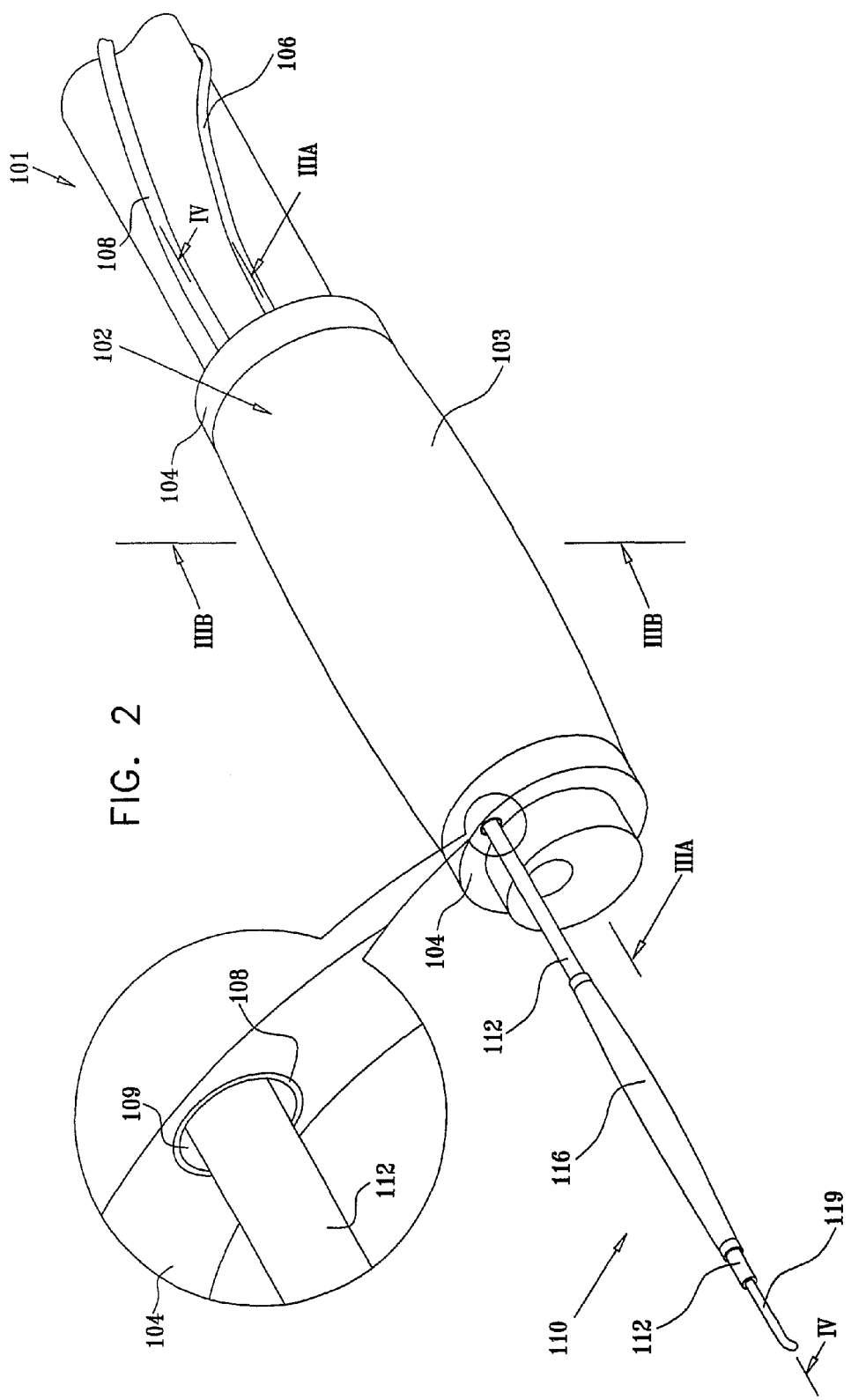

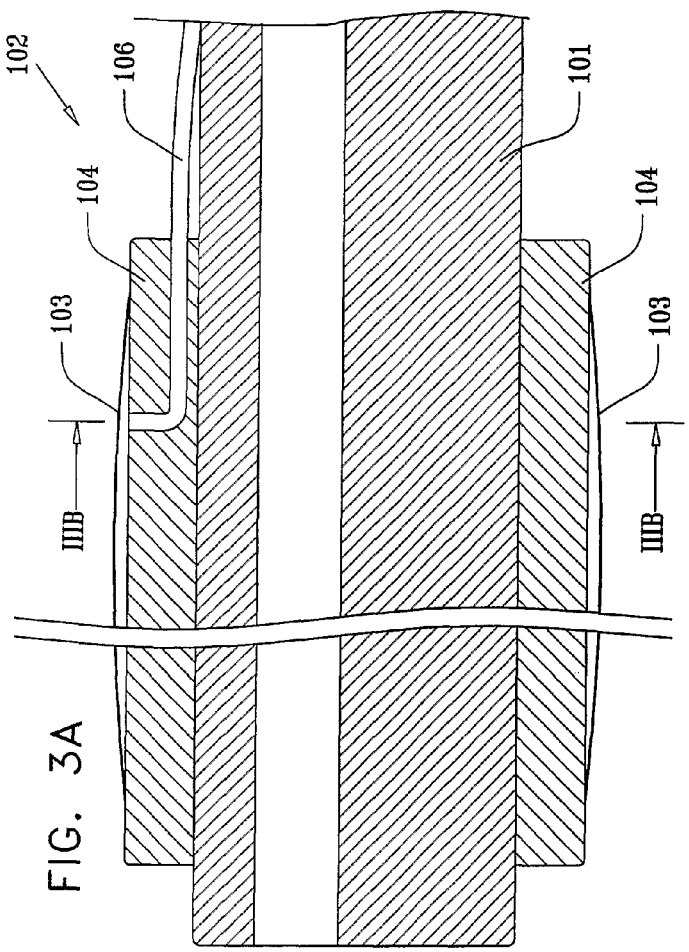
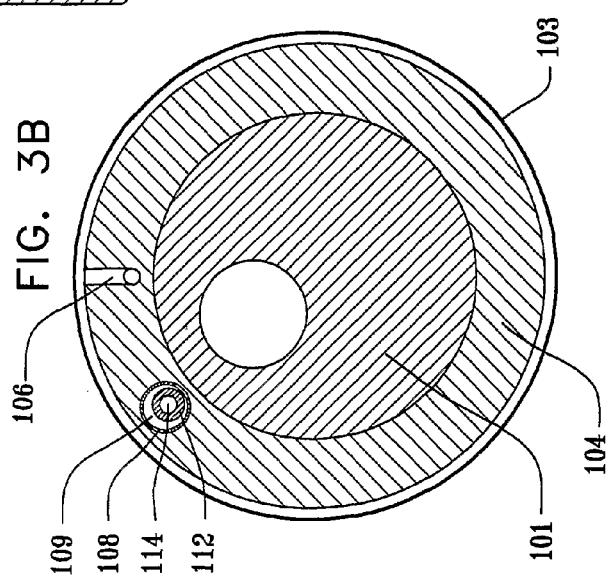

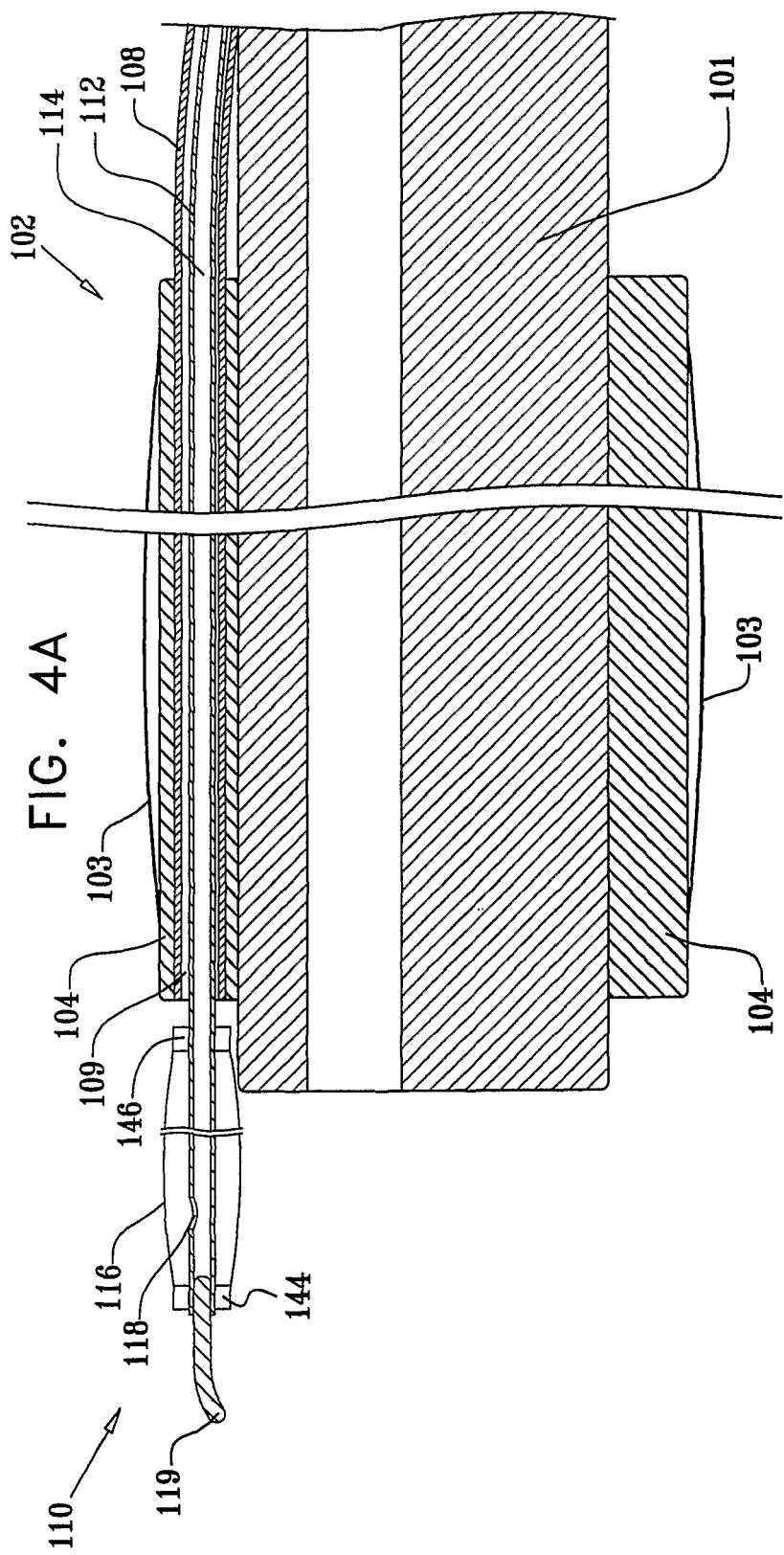

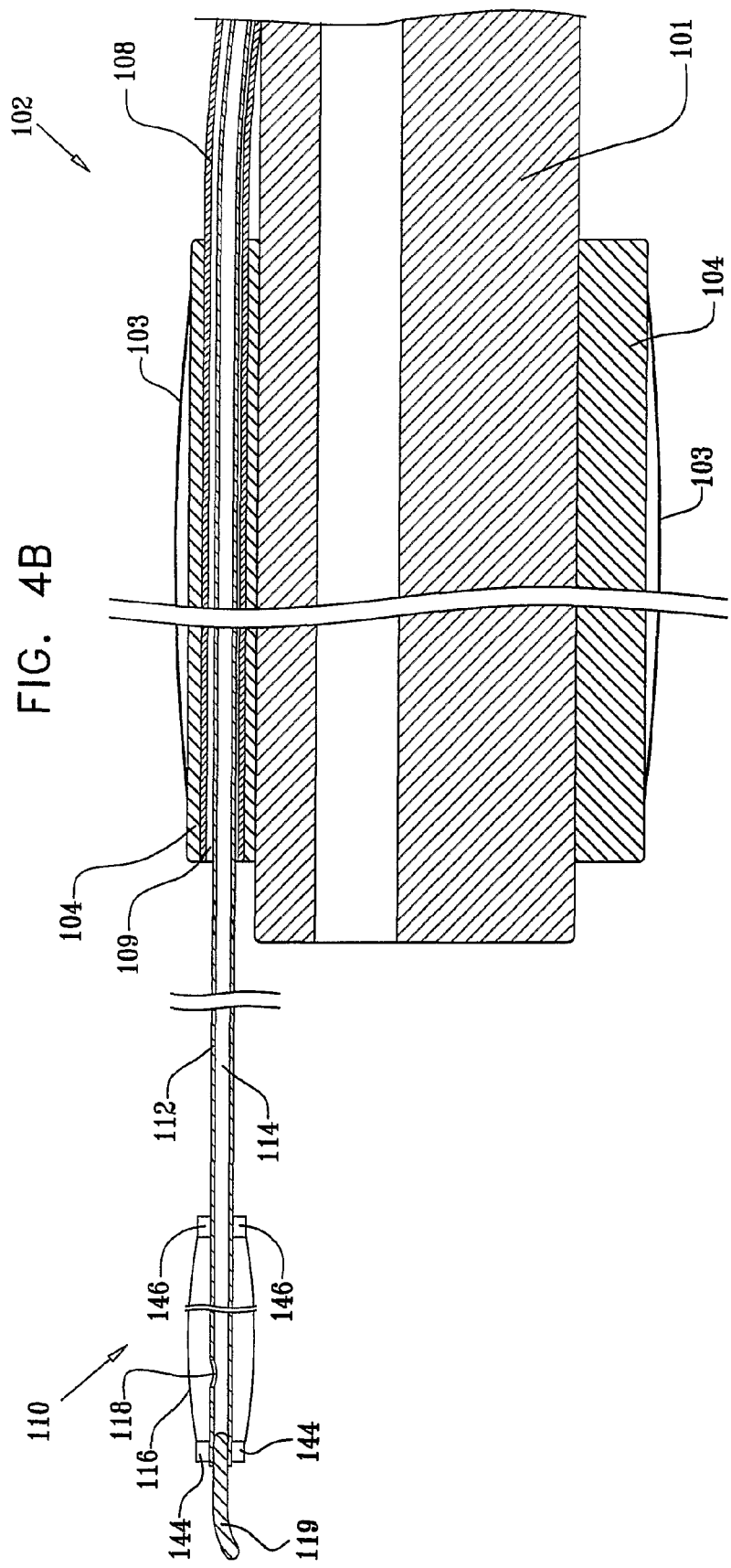

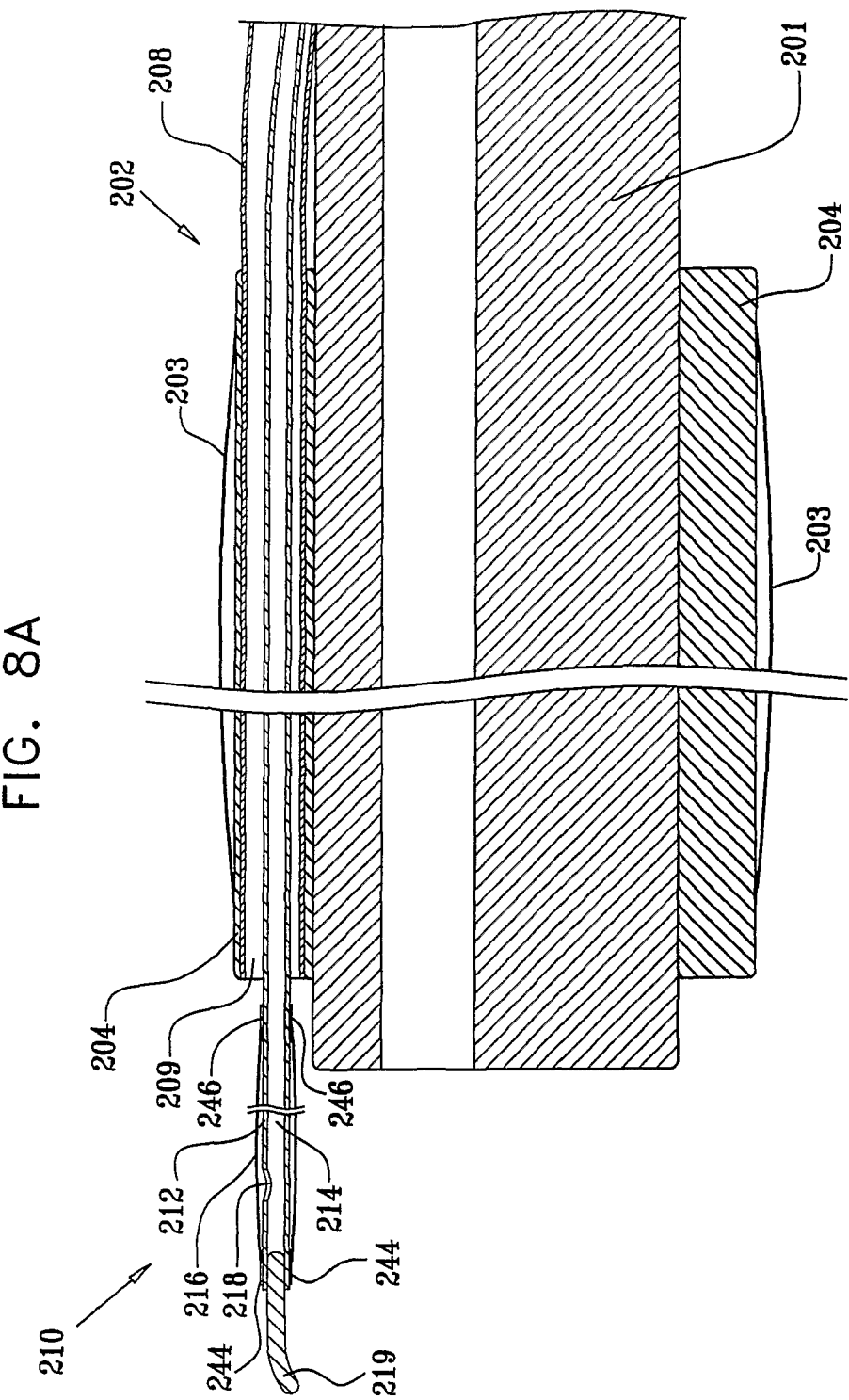

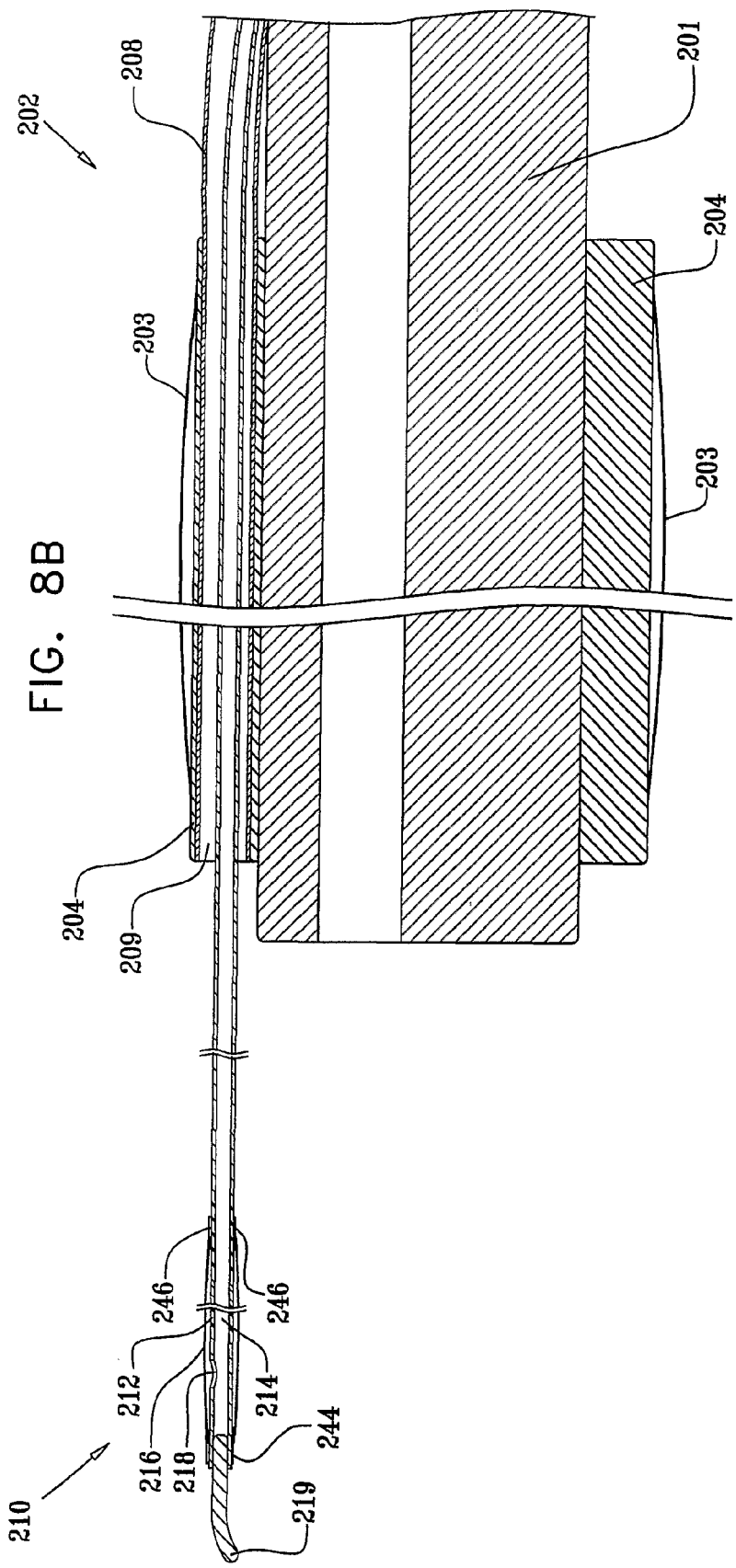

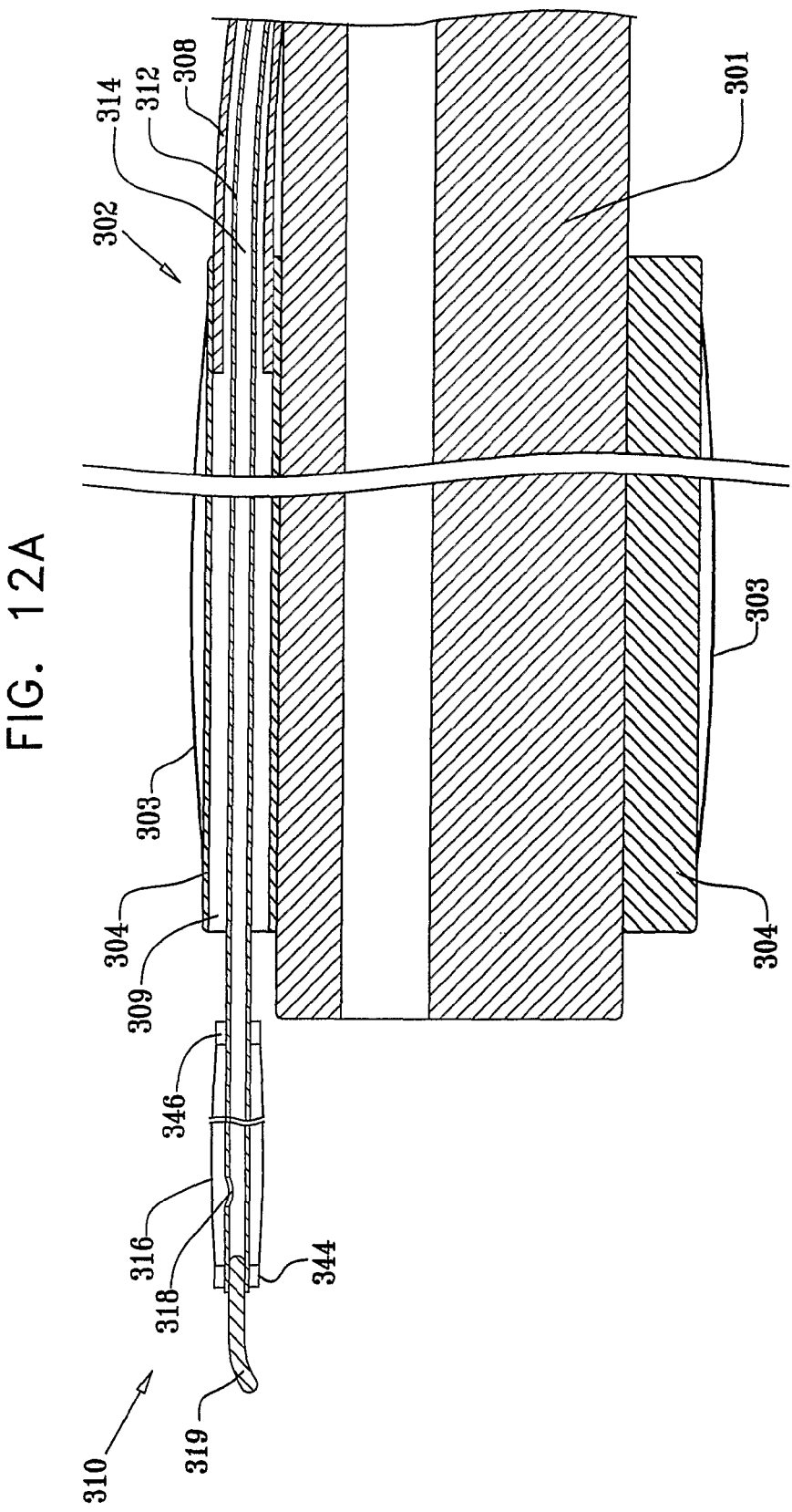

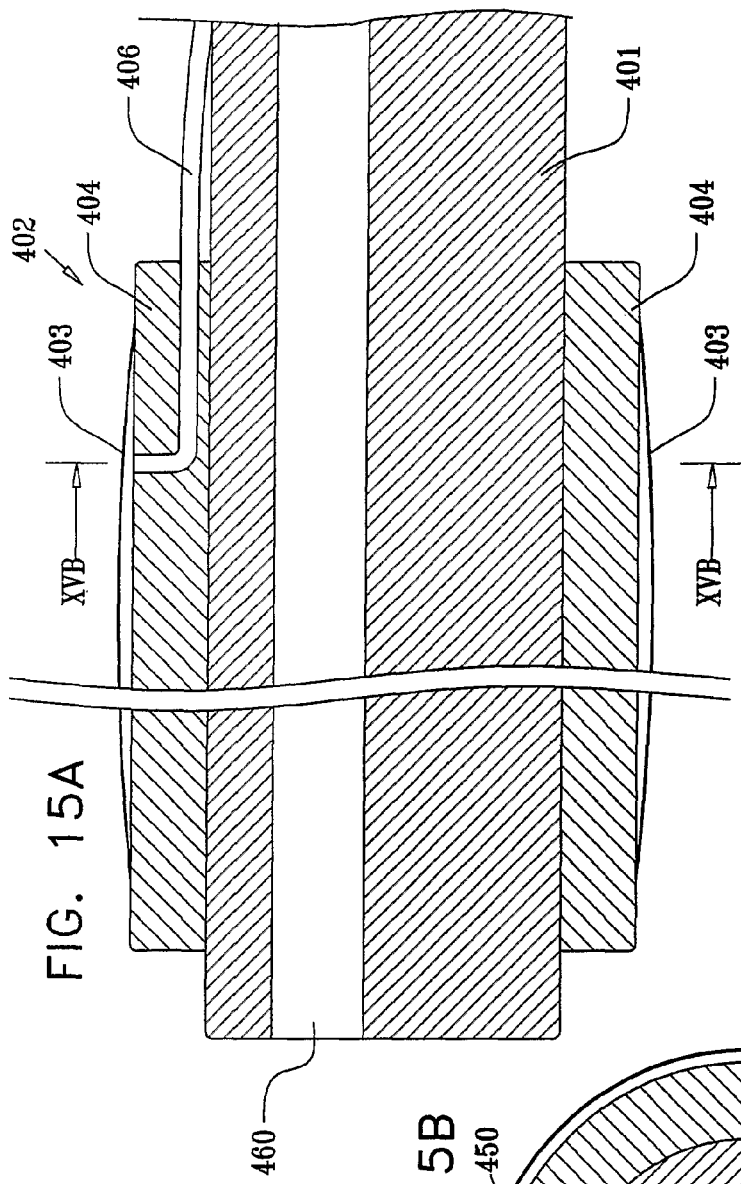
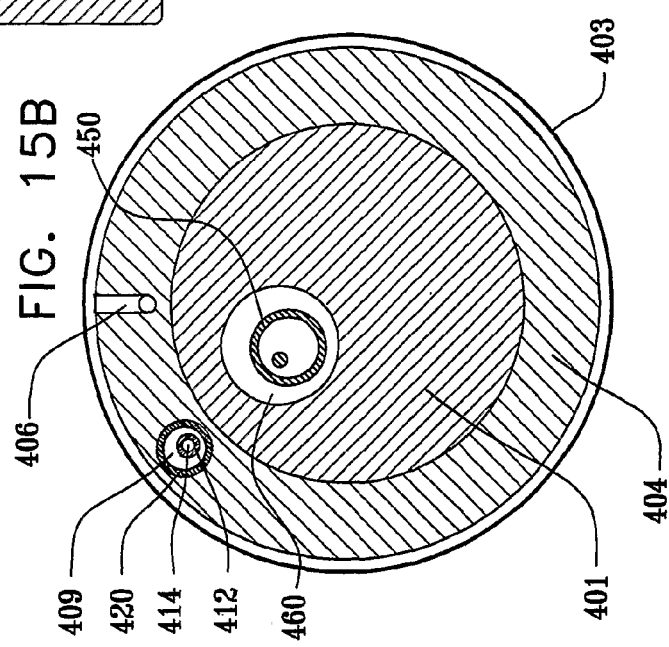
FIG. 15A
FIG. 15B

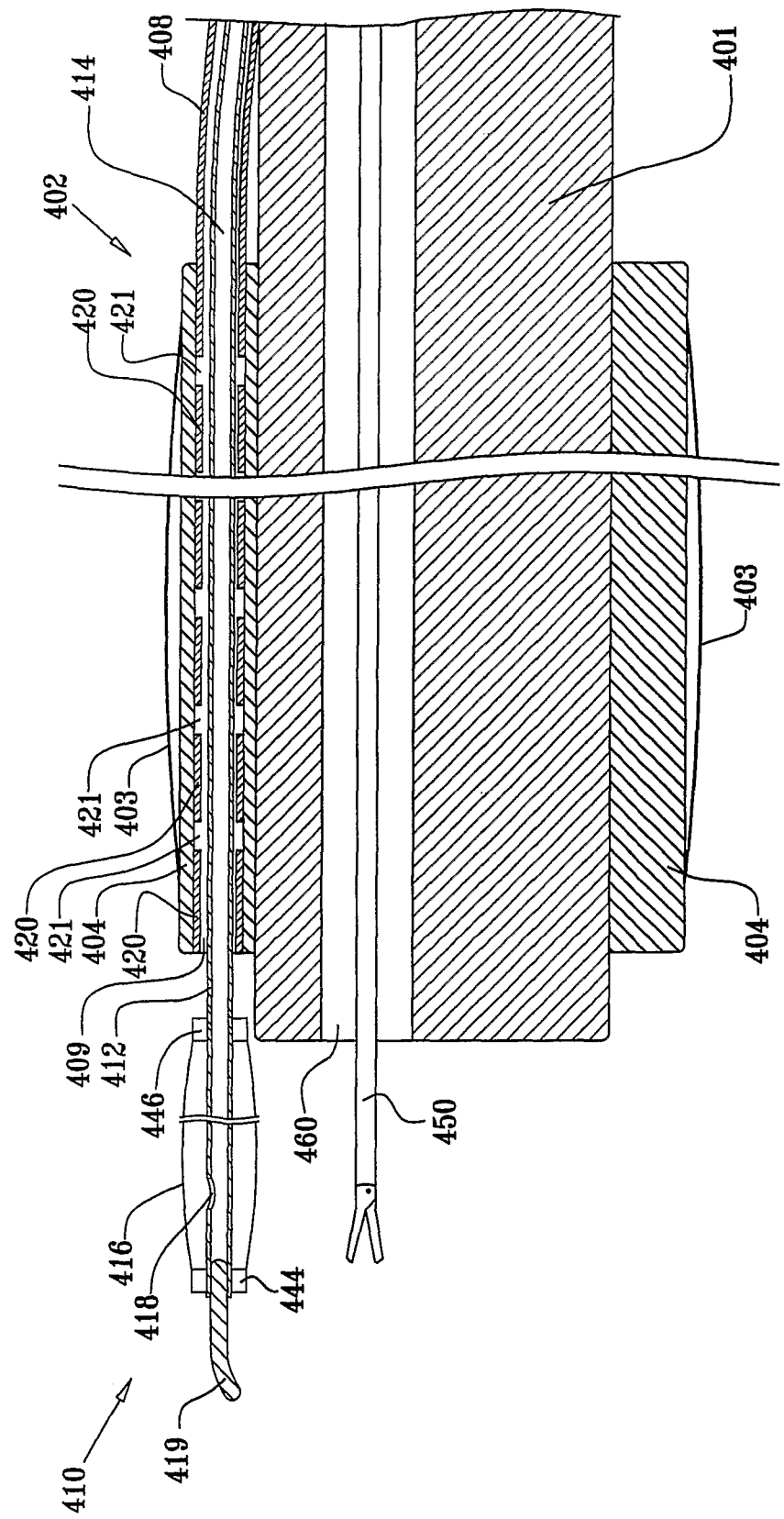

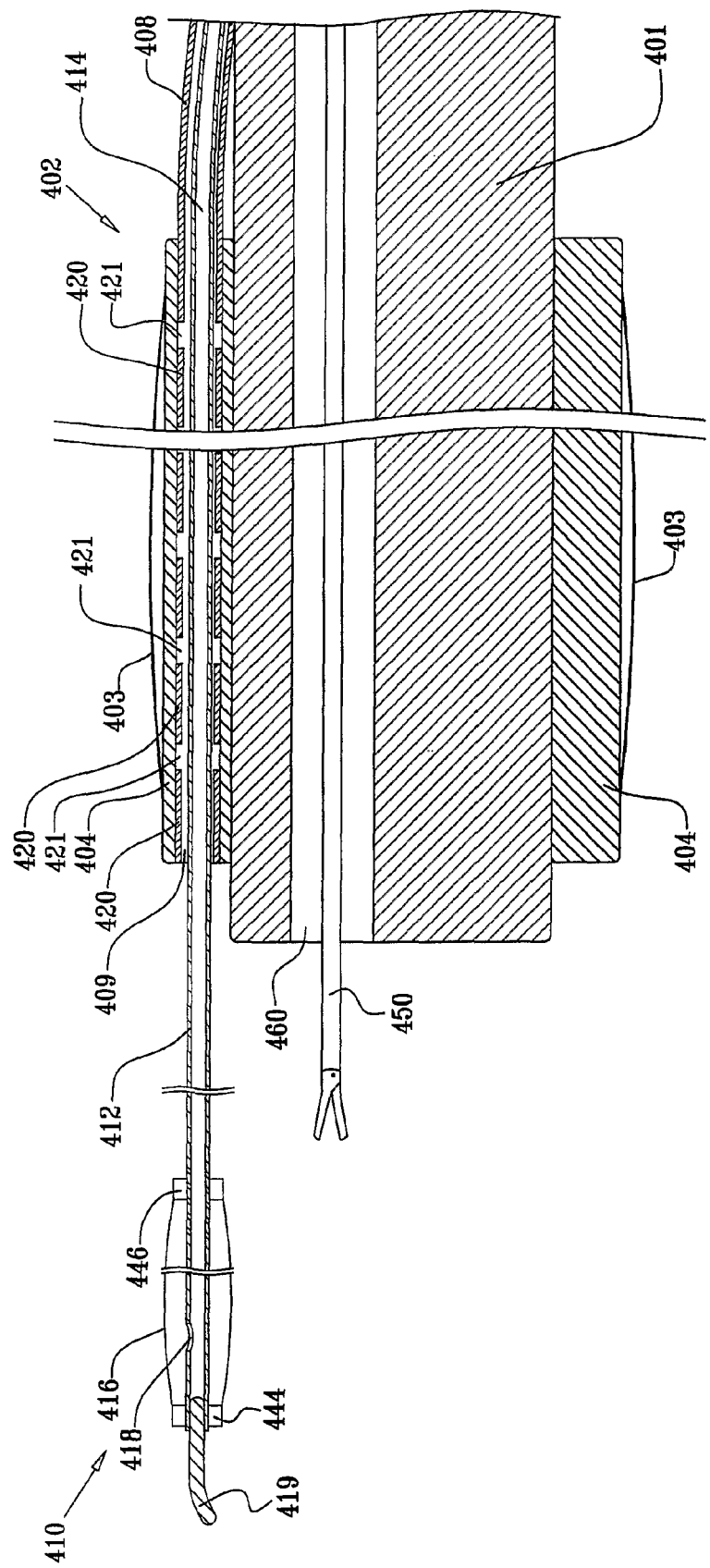

BALLOON GUIDED ENDOSCOPY

FIELD OF THE INVENTION

The present invention relates to endoscopy generally and more particularly to endoscope guiding accessory.

BACKGROUND OF THE INVENTION

The following U.S. Patent Documents are believed to represent the current state of the art:
U.S. Pat. Nos. 4,195,637; 4,616,652 and 6,663,589

SUMMARY OF THE INVENTION

The present invention seeks to provide an endoscope guiding accessory.

There is thus provided in accordance with a preferred embodiment of the present invention apparatus for fluid supply to the interior of a portion of a tubular body portion including at least one first selectably extendible tubular body portion sealing element adapted to be located at a first location along a length of the tubular body portion and at least one second selectably extendible tubular body portion sealing element adapted to be located at a second location along the length, the at least one first selectably extendible tubular body portion sealing element and the at least one second selectably extendible tubular body portion sealing element being adapted to define an intermediate region of the length of the tubular body portion therebetween, a controller adapted for selectably sealing the at least one first and second tubular body portion sealing elements to the tubular body portion and fluid supply functionality adapted for supplying a fluid to the intermediate region.

Preferably, the apparatus for fluid supply also includes an endoscope at least partially extending along the tubular body portion. Preferably, the at least one first and second tubular body portion sealing elements are movable relative to each other along the length.

Preferably, at least one of the at least one first and second tubular body portion sealing elements includes a selectably inflatable balloon. Additionally, the selectably inflatable balloon includes a stretchable balloon. Alternatively, the selectably inflatable balloon includes a polyurethane balloon.

Preferably, the selectably inflatable balloon includes an anchoring balloon.

Preferably, at least one of the at least one first and second tubular body portion sealing elements is mounted on a distal portion of the endoscope. Alternatively or additionally, at least one of the at least one first and second tubular body portion sealing elements is located forward of the endoscope.

Preferably, the apparatus for fluid supply also includes fluid suction functionality for suctioning fluid from the intermediate region.

Preferably, the fluid supply functionality employs an instrument channel of the endoscope.

There is also provided in accordance with another preferred embodiment of the present invention apparatus for fluid supply to the interior of a portion of a tubular body portion including at least one tube including at least first, second and third lumens, a forward selectably inflatable balloon in fluid communication with the first lumen, the forward selectably inflatable balloon being adapted to seal the tubular body portion when inflated, a rear selectably inflatable balloon in fluid communication with the second lumen, the rear selectably inflatable balloon being adapted to seal the tubular body portion when inflated, a fluid supply outlet, located intermediate the forward and rear selectably inflatable balloons, the outlet being in fluid communication with the third lumen, a controller being adapted for selectably inflating the forward and rear selectably inflatable balloons within the tubular body portion, thereby to define an at least partially sealed intermediate region therebetween and fluid supply functionality adapted for supplying a fluid to the at least partially sealed intermediate region.

Preferably, the fluid supply functionality includes an external tube.

Preferably, the fluid supply functionality includes an external tube extending internally of the rear selectably inflatable balloon.

Preferably, the fluid is air.

Preferably, the fluid supply functionality is adapted to inflate the intermediate region of the tubular body portion.

There is further provided in accordance with yet another preferred embodiment of the present invention an endoscope assembly including an endoscope, an external tube extending alongside the endoscope and defining at least one lumen and an endoscope tool adapted to travel through the at least one lumen of the external tube, the endoscope tool including a selectably inflatable balloon.

Preferably, the selectably inflatable balloon is an anchoring balloon.

Preferably, the endoscope tool is bendable forwardly of the external tube. Additionally or alternatively, the endoscope tool is inflatable forwardly of the endoscope. Preferably, the endoscope tool is generally more flexible than the endoscope.

Preferably, the endoscope assembly also includes endoscopy functionality cooperating with the endoscope. Preferably, the endoscope assembly also includes a balloon inflation/deflation controller. Preferably, the external tube is adapted for insertion and removal of the endoscope tool therethrough.

Preferably, the endoscope tool includes a tube portion and a tip portion. Additionally, the tip portion is generally more flexible than the tube portion.

There is even further provided in accordance with still another preferred embodiment of the present invention an endoscope tool including a tube portion, a tip portion and a selectably inflatable balloon, the endoscope tool being adapted to travel through a lumen of an external tube.

Preferably the tip portion is generally more flexible than the tube portion. Additionally or alternatively, the inflatable balloon is mounted on the tube portion. Preferably, an interior portion of the inflatable balloon communicates with an interior portion of the tube portion in order to enable inflation of the inflatable balloon via the tube portion. Alternatively or additionally, the balloon is an anchoring balloon.

There is also provided in accordance with yet another preferred embodiment of the present invention an endoscope assembly including an endoscope, a selectably inflatable balloon mounted onto a distal portion of the endoscope and an external tube extending alongside the endoscope and traversing the selectably inflatable balloon.

Preferably, the external tube passes between the selectably inflatable balloon and the distal portion of the endoscope.

Preferably, the endoscope assembly also includes a tubular sleeve mounted onto the distal portion of the endoscope underlying the selectably inflatable balloon. Preferably, the external tube extends at least partially through a tubular passageway fixed to the distal portion of the endoscope. Additionally, the external tube is slidable within the tubular passageway.

Preferably, the tubular passageway extends through the tubular sleeve. Additionally or alternatively, the tubular passageway includes at least one relatively rigid reinforcement element which permits predetermined bending of the tubular passageway. Preferably, the reinforcement element includes a plurality of mutually spaced relatively rigid elements. Additionally, the mutually spaced relatively rigid elements are tubular.

Preferably, the endoscope assembly also includes a balloon inflation tube communicating with the selectably inflatable balloon. Additionally or alternatively, the selectably inflatable balloon is an anchoring balloon.

Preferably, the endoscope assembly also includes an accessory which is slidably insertable through the external tube to a location forward of the endoscope.

Preferably, the endoscope assembly also includes an endoscope tool at least part of which extends through the external tube, the endoscope tool including a selectably inflatable balloon. Additionally, the endoscope tool is slidably insertable through the external tube. Alternatively, the endoscope tool is not insertable through the external tube.

Preferably, the endoscope tool is slidably insertable through the tubular passageway. Alternatively, the endoscope tool is not insertable through the tubular passageway.

Preferably, the selectably inflatable balloon of the endoscope tool is an anchoring balloon. Additionally or alternatively, the selectably inflatable balloon of the endoscope tool is inflatable forward of the endoscope.

Preferably, the endoscope assembly also includes fluid supply functionality adapted for supplying a fluid via the external tube.

There is yet further provided in accordance with still another preferred embodiment of the present invention apparatus for medical interaction with a tubular body portion including at least one tube including at least first and second lumens, a forward selectably inflatable balloon in fluid communication with the first lumen, the forward selectably inflatable balloon being adapted to engage the tubular body portion when inflated, a controller being adapted for selectably inflating the forward selectably inflatable balloon and an accessory which is slidably insertable through the second lumen to a location rearward of the forward selectably inflatable balloon.

The term "medical interaction" includes for example, inspection, treatment, diagnosis, sampling, removal, marking and any other suitable medical activity.

Preferably, the at least one tube includes an endoscope. Additionally, the endoscope includes an instrument channel which defines the second lumen.

Preferably, the apparatus for medical interaction with a tubular body portion also includes an external tube through which slidably extends one of the at least one tube which defines the first lumen.

Preferably, the at least one tube includes an endoscope and an external tube and a balloon inflation tube defining the first lumen which slidably extends through the external tube. Additionally, the balloon inflation tube is generally more flexible than the endoscope.

Preferably, the forward selectably inflatable balloon is an anchoring balloon. Additionally or alternatively, the forward selectably inflatable balloon is selectably positionable forwardly of the endoscope. Alternatively or additionally, the apparatus for medical interaction with a tubular body portion also includes a rear selectably inflatable balloon. Additionally, the rear selectably inflatable balloon is an anchoring balloon. Alternatively, the rear selectably inflatable balloon is peripherally mounted on a distal portion of an endoscope.

BRIEF DESCRIPTION OF THE DRAWINGS

The present invention will be understood and appreciated more fully from the following detailed description, taken in conjunction with the drawings in which:

FIGS. 2, 3A, 3B, 4A and 4B are respective simplified pictorial and sectional view illustrations of a portion of an endoscope and an auxiliary assembly constructed and operative in accordance with a preferred embodiment of the present invention;

FIGS. 6, 7A, 7B, 8A, 8B, 8C and 8D are respective simplified pictorial and sectional view illustrations of a portion of an endoscope and an auxiliary assembly constructed and operative in accordance with another preferred embodiment of the present invention;

FIGS. 10, 11A, 11B, 12A, 12B and 12C are respective simplified pictorial and sectional view illustrations of a portion of an endoscope and an auxiliary assembly constructed and operative in accordance with yet another preferred embodiment of the present invention;

FIGS. 14, 15A, 15B, 16A and 16B are respective simplified pictorial and sectional view illustrations of a portion of an endoscope and an auxiliary assembly constructed and operative in accordance with further another preferred embodiment of the present invention;

DETAILED DESCRIPTION OF PREFERRED EMBODIMENTS

Figure 1:
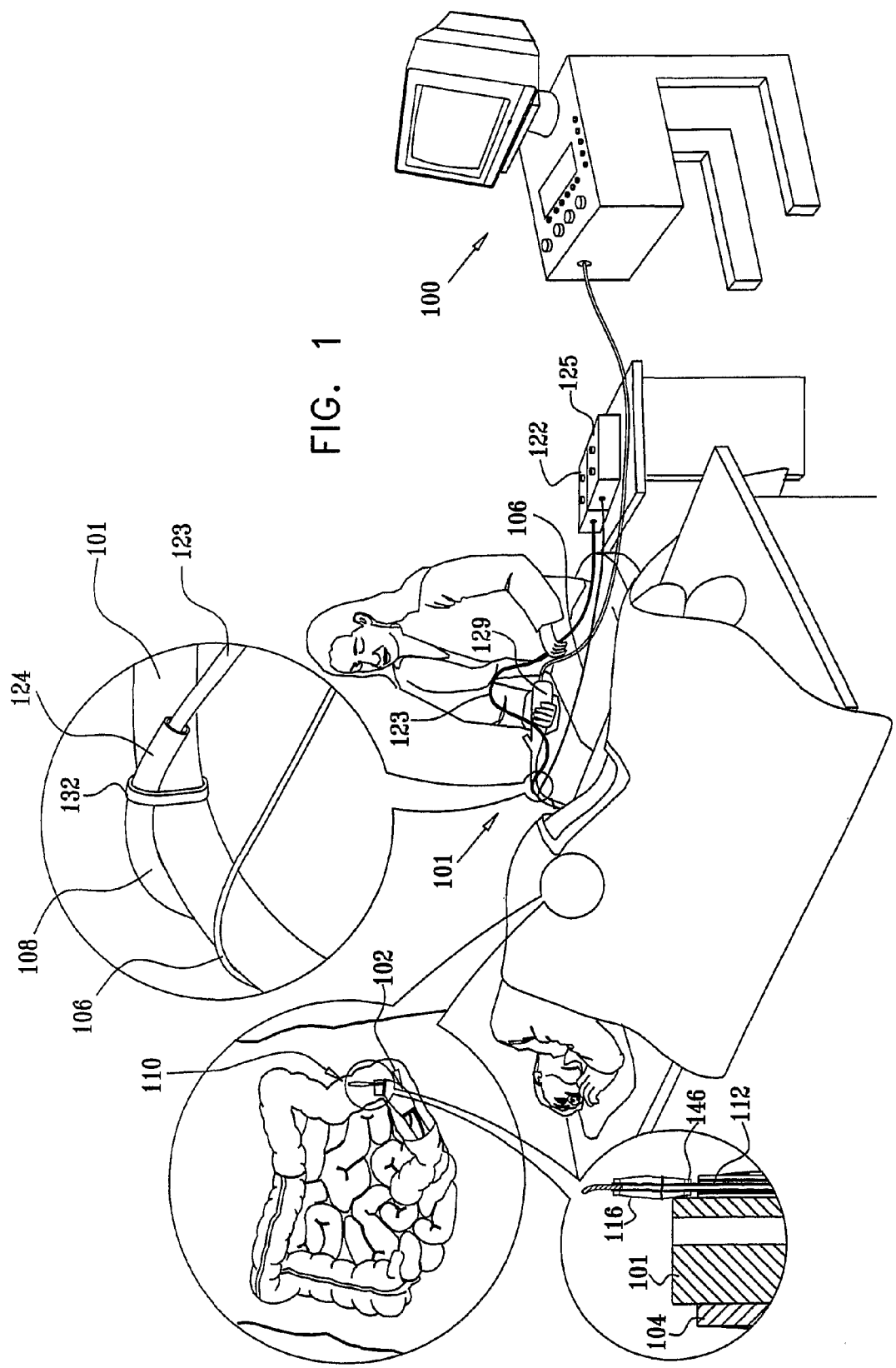
FIG. 1 is a simplified pictorial illustration of an endoscopy system constructed and operative in accordance with a preferred embodiment of the present invention.

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

The term "distal" refers to the remote end of an endoscope, accessory or tool furthest from the operator.

The term "proximal" refers to the end portion of an endoscope, accessory or tool closest to the operator, typically outside an organ or body portion of interest.

Reference is now made to FIGS. 1-4B, which illustrate an endoscopy system constructed and operative in accordance with a preferred embodiment of the present invention and respective simplified pictorial and sectional view illustrations of an auxiliary assembly constructed and operative in accordance with a preferred embodiment of the present invention.

As seen in FIGS. 1-4B a conventional endoscopy system 100, such as a console including a CV-100 video system center, a CLV-U20 light source, a SONY PVM-2030 video monitor, and an OFP flushing pump, all commercially available from Olympus America Inc. of 2 Corporate Center Drive, Melville, N.Y. 11747, USA, is being employed. The system preferably includes a conventional endoscope 101, which forms part of conventional endoscopy system 100 such as a CIF-100 video enteroscope or a CF-Q160AL video colonoscope which is commercially available from Olympus America Inc. of 2 Corporate Center Drive, Melville, N.Y. 11747, USA.

In accordance with a preferred embodiment of the invention, an endoscopy auxiliary assembly 102 comprising a peripheral balloon 103 may be mounted onto endoscope 101 as shown, by means of a tubular sleeve 104 which is fixed over the distal portion of endoscope 101, and is associated with peripheral balloon 103.

It is appreciated that the tubular sleeve 104 may be constructed of a flexible and stretchable material, such as flexible and stretchable silicon, latex or rubber, thereby enabling it to conform with bending of endoscope 101. It is further appreciated that tubular sleeve 104 may have an untensioned inner diameter slightly smaller than the diameter of endoscope 101, thereby allowing it to be pulled and slid over the endoscope 101 when being stretched, while ensuring firm positioning at the desired location on the distal end of endoscope 101.

Alternatively, tubular sleeve 104 may be constructed of a less stretchable material, such as polyurethane or nylon, and of an inner diameter slightly larger than that of endoscope 101, thereby allowing it to be pulled and slid over endoscope 101. Preferably tubular sleeve 104 is formed with a relatively thin wall allowing it to be compliant with the bending of endoscope 101. It is appreciated that once positioned at a desired location, tubular sleeve 104 may be fastened to endoscope 101 by any suitable conventional means, such as a medical adhesive tape.

As illustrated in FIGS. 1-4B, peripheral balloon 103 at least partially overlays tubular sleeve 104, and is fixed thereon at both edges by any suitable conventional means such as an adhesive in order to define a sealed volume therebetween. Preferably inflation and deflation of peripheral balloon 103 is provided via a tube 106 communicating with the interior thereof. Tube 106 may be attached to endoscope 101 at multiple locations along its length by any suitable conventional means such as a medical adhesive tape. Alternatively, tube 106 may be detached from endoscope 101.

It is appreciated that in accordance with a preferred embodiment of the present invention peripheral balloon 103 is generally stretchable, and can be inflated to a diameter about 3-10 times larger than its diameter when not inflated. In accordance with a preferred embodiment of the present invention, useful for small intestine endoscopy, the diameter of peripheral balloon 103 when fully inflated is in the range of 3-4 centimeters.

In a specific embodiment, useful for small intestine endoscopy, the diameter of the peripheral balloon, when it is fully inflated is four centimeters. Preferably, inflation of the peripheral balloon 103 to a diameter less than four centimeters may be achieved using relatively low pressure, such as in the range of 30-70 millibars.

In another specific embodiment, useful for large intestine endoscopy, the diameter of the peripheral balloon, when it is fully inflated is in the range of 4-6 centimeters. In a further embodiment, also useful for large intestine endoscopy, diameter of the peripheral balloon, when it is fully inflated is six centimeters. Preferably, inflation of the peripheral balloon 103 to a diameter less than six centimeters may be achieved using relatively low pressure, such as in the range of 30-70 millibars.

It is appreciated that in accordance with a preferred embodiment of the present invention, useful for in vivo inspection of a generally tubular body portion having a variable cross-sectional diameter, the expansion diameter range of peripheral balloon 103 is larger than the maximum cross-sectional diameter of the generally tubular body portion, thereby enabling engagement of expanded peripheral balloon 103 with the interior surface of the generally tubular body portion, and anchoring of the endoscope 101 thereto. Preferably, peripheral balloon 103 is a relatively soft, highly compliant balloon, operative to at least partially conform to the shape of the interior surface of the generally tubular body portion when in engagement therewith.

It is appreciated that peripheral balloon 103 may be formed of suitable well-known stretchable materials such as latex, flexible silicon, or highly flexible nylon. Alternatively, peripheral balloon 103 may be formed of polyurethane, which is less stretchable and conforming than latex, flexible silicon or highly flexible nylon. Preferably, the diameter of peripheral balloon 103 is sufficient to ensure tight anchoring at any part of the generally tubular body portion.

In a preferred embodiment of the present invention, endoscopy auxiliary assembly 102 may comprise at least one external tube 108. External tube 108 may be attached to the endoscope 101 at multiple locations along its length by any suitable conventional means such as a medical adhesive tape. Alternatively, external tube 108 may be detached from the endoscope 101.

It is appreciated that external tube 108 may be flexible and highly bendable, allowing it to be compliant with the bending of endoscope 101. It is further appreciated that external tube 108 may be constructed of a low friction material, such as TEFLON®.

In a preferred embodiment of the present invention, external tube 108 may be inserted through a tubular passageway 109, which extends longitudinally within tubular sleeve 104. Alternatively, the tubular passageway may be located interiorly of the sleeve but external to the endoscope 101. External tube 108 may be inserted fully or partially through tubular passageway 109, and may be fixed to tubular sleeve 104 by any conventional means, such as by friction or by use of a suitable adhesive. Alternatively, external tube 108 may be slidable with respect to tubular passageway 109.

An endoscope tool 110, constructed and operative in accordance with a preferred embodiment of the present invention, extends through external tube 108. Endoscope tool 110 preferably comprises a guiding tube 112, which includes at least a first lumen 114 for inflation and deflation of a balloon 116 via an inflation aperture 118. Preferably, the cross-sectional area of guiding tube 112 is sufficiently smaller than that of external tube 108, so as to allow generally free passage of guiding tube 112 through external tube 108, particularly when the external tube 108 is in a bent or curved state, and to allow supply of fluid for inflation or other uses and draining of fluid therethrough.

It is appreciated that guiding tube 112 may be flexible and highly bendable, so as to allow its compliance with the bending of endoscope 101 and with the curves of the intestine. It is further appreciated that guiding tube 112 may be constructed of a low friction material, such as TEFLON®.

Preferably, guiding tube 112 is sealed at its distal end forward of balloon 116 in any suitable manner such as by mechanical sealing or use of an appropriate adhesive, to facilitate inflation and deflation of balloon 116 through guiding tube 112.

Preferably, endoscope tool 110 comprises a tip portion 119 located distally of balloon 116. The tip portion 119 may be made of a highly flexible tube, such as a TYGON® tube, with a diameter of 1.5 millimeters. The tip portion 119 may be connected to the distal end of guiding tube 112 by any conventional means such as a suitable adhesive. In a preferred embodiment of the present invention the length of tip portion 119 is 20-30 millimeters.

It is appreciated that the high bendability of tip portion 119 prevents endoscope tool 110 from getting stuck in obstacles and bends as it advances through the generally tubular body portion, forward of endoscope 101.

It is appreciated that in accordance with a preferred embodiment of the present invention the endoscope tool 110 and the guiding tube 112 are substantially more flexible than endoscope 101.

It is further appreciated that in accordance with a preferred embodiment of the present invention the tube 106 is substantially more flexible than endoscope 101.

It is appreciated that in accordance with yet another preferred embodiment of the present invention the external tube 108 is substantially more flexible than endoscope 101.

It is appreciated that in accordance with a preferred embodiment of the present invention balloon 116 is generally stretchable, and can be inflated to a diameter about 5-20 times larger than its diameter when not inflated. In a specific embodiment, useful for small intestine endoscopy, the balloon diameter when fully inflated is in the range of 3-4 centimeters. In a specific embodiment, useful for small intestine endoscopy, the balloon diameter when fully inflated is four centimeters. Preferably, inflation of the balloon 116 to a diameter less than four centimeters may be achieved using relatively low pressure, such as in the range of 30-70 millibars. In accordance with another preferred embodiment of the present invention, useful for large intestine endoscopy, the balloon diameter when fully inflated is in the range of 4-6 centimeters. In another specific embodiment, useful for large intestine endoscopy, the balloon diameter when fully inflated is six centimeters. Preferably, inflation of the balloon 116 to a diameter less than six centimeters may be achieved using relatively low pressure, such as in the range of 30-70 millibars.

It is appreciated that in accordance with a preferred embodiment of the present invention which is particularly useful for in vivo inspection of a generally tubular body portion having a variable cross-sectional diameter, the expansion range of the diameter of balloon 116 is larger than the maximum cross-sectional diameter of the generally tubular body portion, thereby enabling engagement of expanded balloon 116 with the interior surface of the generally tubular body portion, and anchoring of the endoscope tool 110 thereto. Preferably, balloon 116 is a relatively soft, highly compliant balloon, operative to at least partially conform to the shape of the interior surface of the generally tubular body portion when in engagement therewith.

It is appreciated that balloon 116 may be formed of well-known stretchable materials such as latex, flexible silicon, or highly flexible nylon. Alternatively, balloon 116 may be formed of polyurethane, which is less stretchable and conforming than latex, flexible silicon or highly flexible nylon. Preferably, the diameter of balloon 116 is sufficient to ensure tight anchoring at any location in the generally tubular body portion.

As seen in FIG. 1, the endoscope tool 110 preferably includes a balloon inflation/deflation control interface 122 which communicates with guiding tube 112 at a proximal portion 123 thereof which extends outwardly of a proximal end 124 of external tube 108 and governs inflation and deflation of balloon 116. Additionally, there is preferably provided a peripheral balloon inflation/deflation control interface 125, which communicates with tube 106 and governs inflation and deflation of peripheral balloon 103.

Preferably, proximal end 124 of external tube 108 is fixed to the proximal portion of endoscope 101 adjacent to an operator control 129 of endoscope 101, by a band 132 or by any other suitable conventional means, such as a clips or medical adhesive tape. Preferably, the operator positions balloon 116 at a desired location forward of the distal end of endoscope 101 within the generally tubular body portion, by controlled pulling or pushing of the proximal portion 123 of guiding tube 112, relative to the proximal end 124 of external tube 108.

FIG. 4A shows rearward positioning of endoscope tool 110 in which the balloon 116 is located just ahead of the distal end of endoscope 101. The rearward positioning is preferably accomplished by pulling the proximal portion 123 of guiding tube 112 rearwardly relative to the proximal end 124 of external tube 108.

FIG. 4B shows forward positioning of endoscope tool 110 in which the balloon 116 is located a substantial distance forward of the distal end of endoscope 101. The forward positioning is preferably accomplished by pushing the proximal portion 123 of guiding tube 112 forwardly relative to the proximal end 124 of external tube 108.

It is appreciated that controlled positioning of the endoscope tool 110 at desired distances forward of the distal end of endoscope 101 may be achieved by suitable controlled positioning of the proximal portion 123 of guiding tube 112 relative to the proximal end 124 of external tube 108.

It is appreciated that in accordance with a preferred embodiment of the present invention useful for in vivo inspection of a generally tubular body portion having a variable cross-sectional diameter, balloon 116 may be controllably positioned in a range of 0-45 centimeters forward of the distal end of endoscope 101.

As seen in FIGS. 4A and 4B, balloon 116 is fixed to guiding tube 112 via a forward balloon sleeve portion 144 and via a rear balloon sleeve portion 146, both of which are preferably integrally formed with balloon 116. As seen in FIG. 4A, the outer cross sectional diameter of rear sleeve portion 146 is larger than the inner cross sectional diameter of external tube 108 and larger than the inner cross sectional diameter of tubular passageway 109, thereby preventing balloon 116 from being inserted through external tube 108 and through tubular passageway 109.

It is appreciated that rear sleeve portion 146 may function as a stopper that prevents further pulling of guiding tube 112 when rear sleeve portion 146 is in contact with tubular sleeve 104 or with external tube 108.

Reference is now made to FIGS. 5-8D, which are respectively a simplified pictorial illustration of an endoscopy system constructed and operative in accordance with another preferred embodiment of the present invention and respective simplified pictorial and sectional view illustrations of an auxiliary assembly constructed and operative in accordance with another preferred embodiment of the present invention.

As seen in FIGS. 5-8D a conventional endoscopy system 200, such as a console including a CV-100 video system center, a CLV-U20 light source, a SONY PVM-2030 video monitor, and an OFP flushing pump, all commercially available from Olympus America Inc. of 2 Corporate Center Drive, Melville, N.Y. 11747, USA, is being employed. The system preferably includes a conventional endoscope 201, which forms part of conventional endoscopy system 200 such as a CIF-100 video enteroscope or a CF-Q160AL video colonoscope which is commercially available from Olympus America Inc. of 2 Corporate Center Drive, Melville, N.Y. 11747, USA.

In accordance with a preferred embodiment of the invention, an endoscopy auxiliary assembly 202 comprising a peripheral balloon 203 may be mounted onto endoscope 201 as shown, by means of a tubular sleeve 204 which is fixed over the distal portion of endoscope 201, and is associated with peripheral balloon 203. It is appreciated that the tubular sleeve 204 may be constructed of a flexible and stretchable material, such as flexible and stretchable silicon, latex or rubber, thereby enabling it to conform with bending of endoscope 201. It is further appreciated that tubular sleeve 204 may have a an untensioned inner diameter slightly smaller than the diameter of endoscope 201, thereby allowing it to be pulled and slid over the endoscope 201 when being stretched, while ensuring firm positioning at the desired location on the distal end of endoscope 201.

Alternatively, tubular sleeve 204 may be constructed of a less stretchable material, such as polyurethane or nylon, and of an inner diameter slightly larger than that of endoscope 201, thereby allowing it to be pulled and slid over endoscope 201. Preferably tubular sleeve 204 is formed with a relatively thin wall allowing it to be compliant with the bending of endoscope 201. It is appreciated that once positioned at a desired location, tubular sleeve 204 may be fastened to endoscope 201 by any suitable conventional means, such as a medical adhesive tape.

As illustrated in FIGS. 5-8D, peripheral balloon 203 at least partially overlays tubular sleeve 204, and is fixed thereon at both edges by any suitable conventional means such as an adhesive in order to define a sealed volume therebetween. Preferably inflation and deflation of peripheral balloon 203 is provided via a tube 206 communicating with the interior thereof. Tube 206 may be attached to endoscope 201 at multiple locations along its length by any suitable conventional means such as a medical adhesive tape. Alternatively, tube 206 may be detached from endoscope 201.

It is appreciated that in accordance with a preferred embodiment of the present invention peripheral balloon 203 is generally stretchable, and can be inflated to a diameter about 3-10 times larger than its diameter when not inflated. In accordance with a preferred embodiment of the present invention, useful for small intestine endoscopy, the diameter of peripheral balloon 203 when fully inflated is in the range of 3-4 centimeters. In a specific embodiment, useful for small intestine endoscopy, the diameter of the peripheral balloon diameter when it is fully inflated is four centimeters. Preferably, inflation of the peripheral balloon 203 to a diameter less than four centimeters may be achieved using relatively low pressure, such as in the range of 30-70 millibars.

In another specific embodiment useful for large intestine endoscopy, the diameter of the peripheral balloon when it is fully inflated is in the range of 4-6 centimeters. In a further embodiment, also useful for large intestine endoscopy, diameter of the peripheral balloon, when it is fully inflated is six centimeters. Preferably, inflation of the peripheral balloon 203 to a diameter less than six centimeters may be achieved using relatively low pressure, such as in the range of 30-70 millibars.

It is appreciated that in accordance with a preferred embodiment of the present invention, useful for in vivo inspection of a generally tubular body portion having a variable cross-sectional diameter, the expansion diameter range of peripheral balloon 203 is larger than the maximum cross-sectional diameter of the generally tubular body portion, thereby enabling engagement of expanded peripheral balloon 203 with the interior surface of the generally tubular body portion, and anchoring of the endoscope 201 thereto. Preferably, peripheral balloon 203 is a relatively soft, highly compliant balloon, operative to at least partially conform to the shape of the interior surface of the generally tubular body portion when in engagement therewith.

It is appreciated that peripheral balloon 203 may be formed of suitable well-known stretchable materials such as latex, flexible silicon, or highly flexible nylon. Alternatively, peripheral balloon 203 may be formed of polyurethane, which is less stretchable and conforming than latex, flexible silicon or highly flexible nylon. Preferably, the diameter of peripheral balloon 203 is sufficient to ensure tight anchoring at any part of the generally tubular body portion.

In a preferred embodiment of the present invention, endoscopy auxiliary assembly 202 may comprise at least one external tube 208. External tube 208 may be attached to the endoscope 201 at multiple locations along its length by any suitable conventional means such as a medical adhesive tape. Alternatively, external tube 208 may be detached from the endoscope 201.

It is appreciated that external tube 208 may be flexible and highly bendable, allowing it to be compliant with the bending of endoscope 201. It is further appreciated that external tube 208 may be constructed of a low friction material, such as TEFLON®.

In a preferred embodiment of the present invention, external tube 208 may be inserted through a tubular passageway 209, which extends longitudinally within tubular sleeve 204. Alternatively, the tubular passageway may be located interiorly of the sleeve but external to the endoscope 201. External tube 208 may be inserted fully or partially through tubular passageway 209, and may be fixed to tubular sleeve 204 by any conventional means, such as by friction or by use of a suitable adhesive. Alternatively, external tube 208 may be slidable with respect to tubular passageway 209.

An endoscope tool 210, constructed and operative in accordance with a preferred embodiment of the present invention, extends through external tube 208. Endoscope tool 210 preferably comprises a guiding tube 212, which includes at least a first lumen 214 for inflation and deflation of a balloon 216 via an inflation aperture 218. Preferably, the cross-sectional area of guiding tube 212 is sufficiently smaller than that of external tube 208, so as to allow generally free passage of guiding tube 212 through external tube 208, particularly when the external tube 208 is in a bent or curved state, and to allow supply of fluid for inflation or other uses and draining of fluid therethrough.

It is appreciated that guiding tube 212 may be flexible and highly bendable, so as to allow its compliance with the bending of endoscope 201 and with the curves of the intestine. It is further appreciated that guiding tube 212 may be constructed of a low friction material, such as TEFLON®.

Preferably, guiding tube 212 is sealed at its distal end forward of balloon 216 in any suitable manner such as by mechanical sealing or use of an appropriate adhesive, to facilitate inflation and deflation of balloon 216 through guiding tube 212.

Preferably, endoscope tool 210 may comprise a tip portion 219 located distally of balloon 216. The tip portion 219 may be made of a highly flexible tube, such as a TYGON® tube, with a diameter of 1.5 millimeters. The tip portion 219 may be connected to the distal end of guiding tube 212 by any conventional means such as a suitable adhesive. In a preferred embodiment of the present invention the length of tip portion 219 is 20-30 millimeters.

It is appreciated that the high bendability of tip portion 219 prevents endoscope tool 210 from getting stuck in obstacles and bends as it advances through the generally tubular body portion, forward of endoscope 201.

It is appreciated that in accordance with a preferred embodiment of the present invention the endoscope tool 210 and the guiding tube 212 are substantially more flexible than endoscope 201.

It is further appreciated that in accordance with a preferred embodiment of the present invention the tube 206 is substantially more flexible than endoscope 201.

It is appreciated that in accordance with yet another preferred embodiment of the present invention the external tube 208 is substantially more flexible than endoscope 201.

It is appreciated that in accordance with a preferred embodiment of the present invention the balloon 216 is generally stretchable, and can be inflated to a diameter about 5-20 times larger than its diameter when not inflated. In a specific embodiment useful for small intestine endoscopy, the balloon diameter when fully inflated is in the range of 3-4 centimeters. In a specific embodiment, useful for small intestine endoscopy, the balloon diameter when fully inflated is four centimeters. Preferably, inflation of the balloon 216 to a diameter less than four centimeters may be achieved using relatively low pressure, such as in the range of 30-70 millibars.

In another preferred embodiment of the present invention, useful for large intestine endoscopy, the balloon diameter when fully inflated is in the range of 4-6 centimeters. In another specific embodiment, useful for large intestine endoscopy, the balloon diameter when fully inflated is six centimeters. Preferably, inflation of the balloon 216 to a diameter less than six centimeters may be achieved using relatively low pressure, such as in the range of 30-70 millibars.

It is appreciated that in accordance with a preferred embodiment of the present invention which is particularly useful for in vivo inspection of a generally tubular body portion having a variable cross-sectional diameter, the expansion range of the diameter of balloon 216 is larger than the maximum cross-sectional diameter of the generally tubular body portion, thereby enabling engagement of expanded balloon 216 with the interior surface of the generally tubular body portion, and anchoring of the endoscope tool 210 thereto. Preferably, balloon 216 is a relatively soft, highly compliant balloon, operative to at least partially conform to the shape of the interior surface of the generally tubular body portion when in engagement therewith.

It is appreciated that balloon 216 may be formed of well-known stretchable materials such as latex, flexible silicon, or highly flexible nylon. Alternatively, balloon 216 may be formed of polyurethane, which is less stretchable and conforming than latex, flexible silicon or highly flexible nylon. Preferably, the diameter of balloon 216 is sufficient to ensure tight anchoring at any location in the generally tubular body portion.

Figure 5:
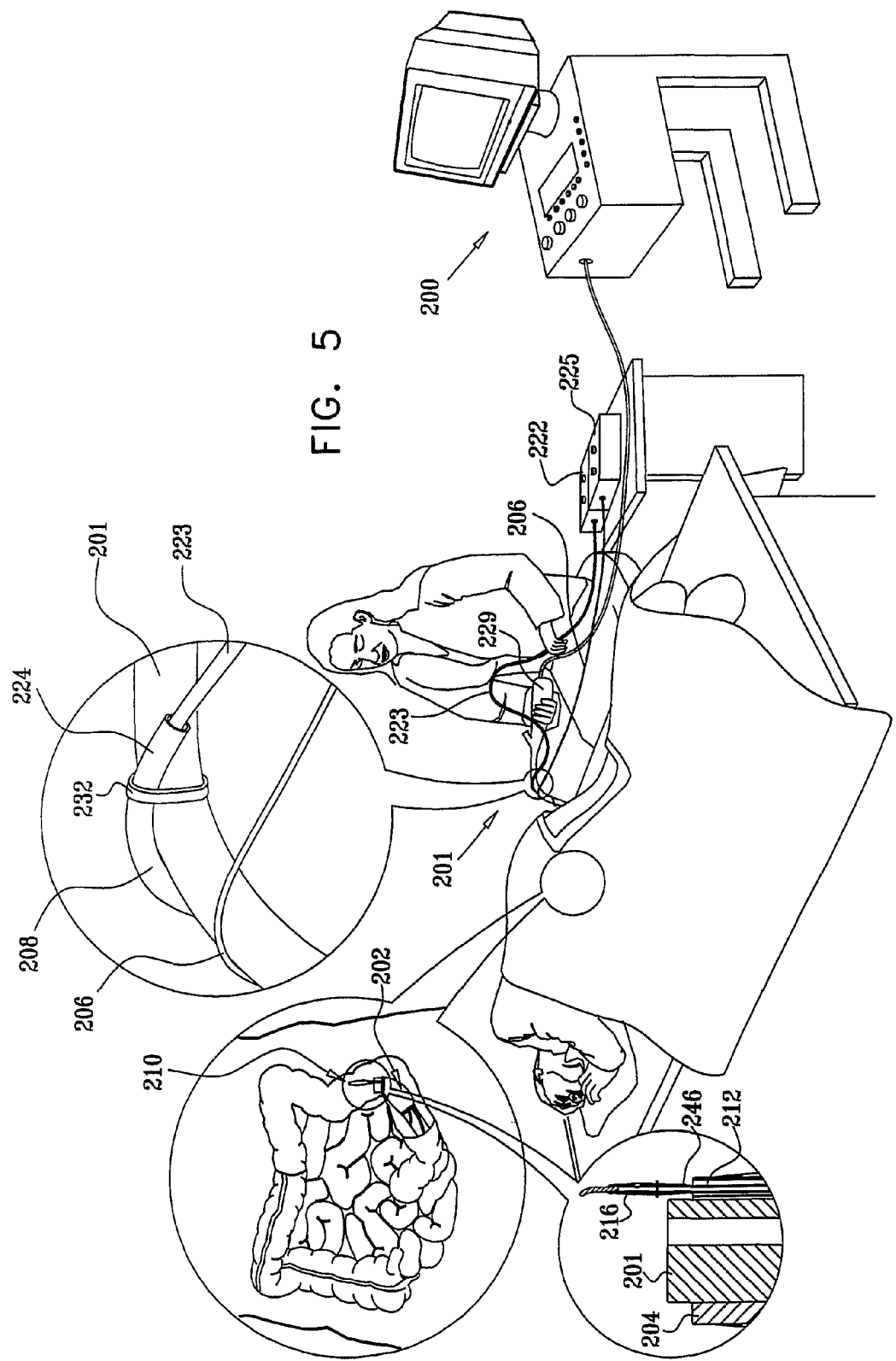
FIG. 5 is a simplified pictorial illustration of an endoscopy system constructed and operative in accordance with another preferred embodiment of the present invention.
Figure 6:
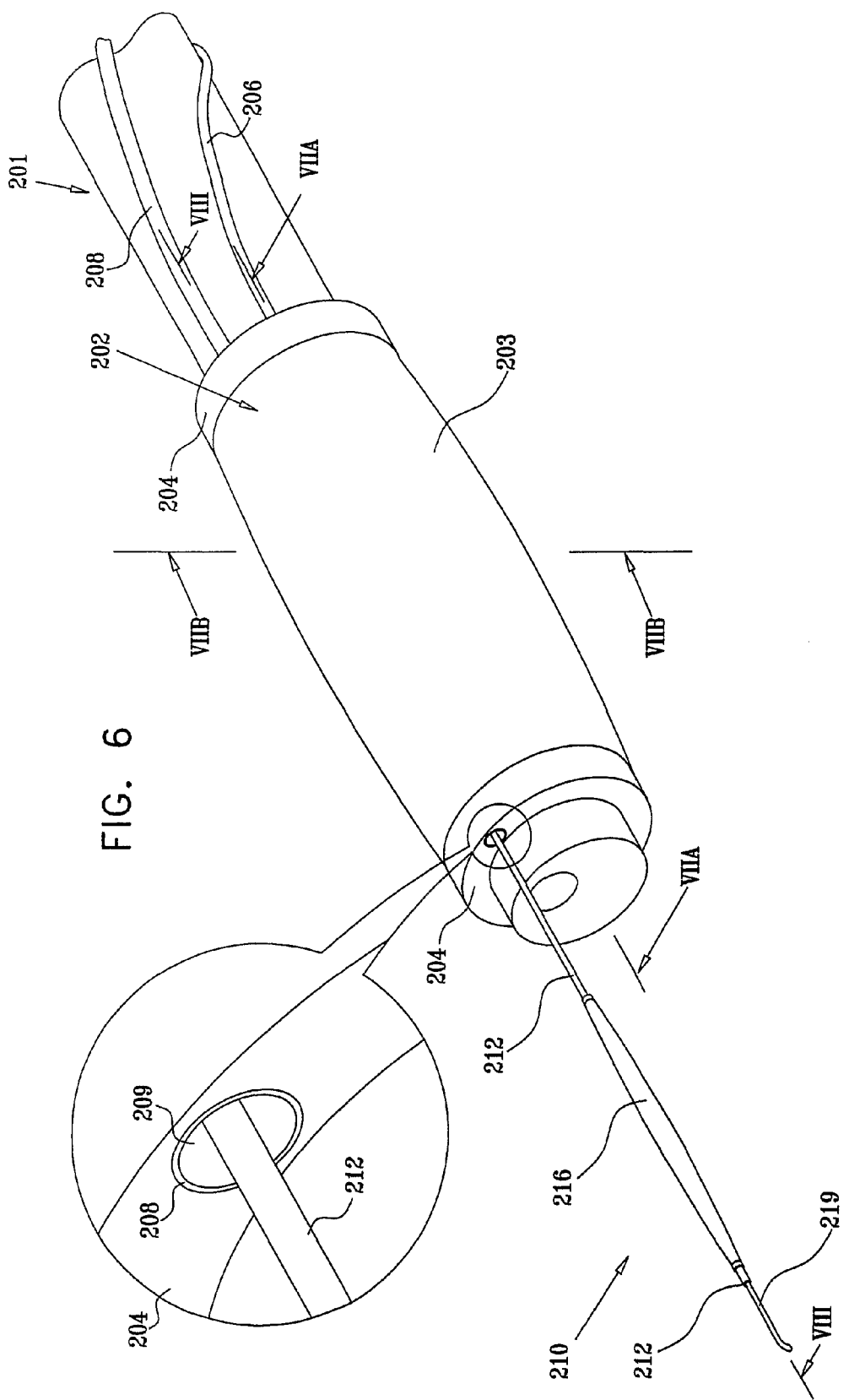
Figure 7A:
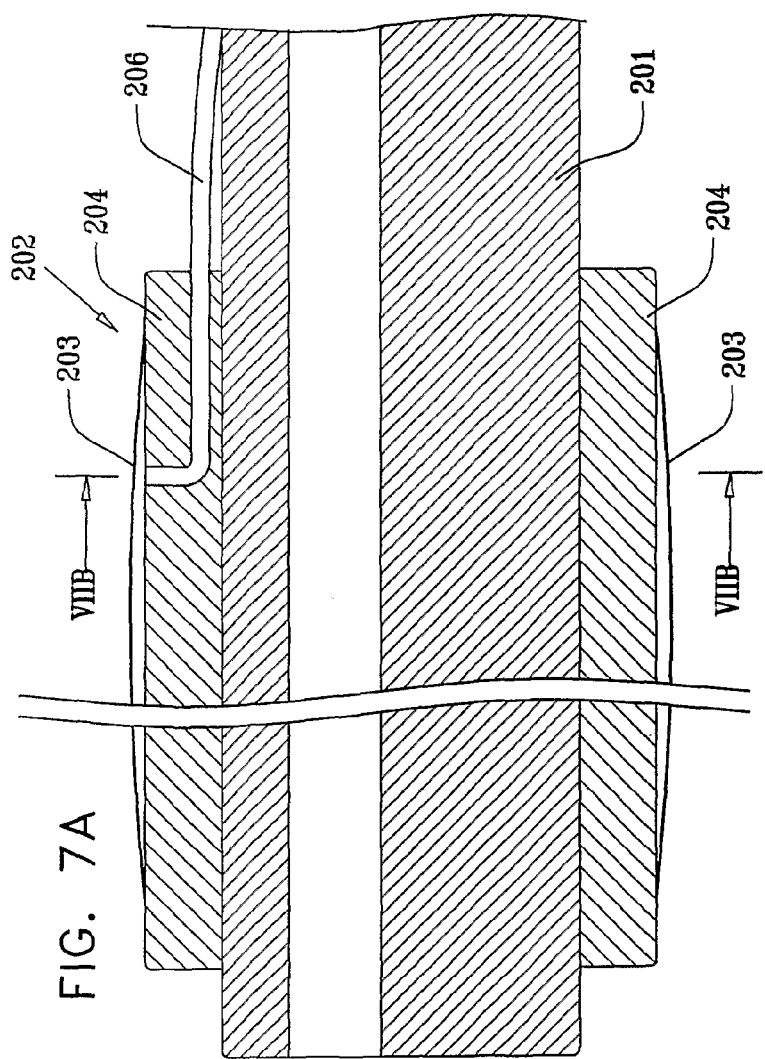
Figure 7B:
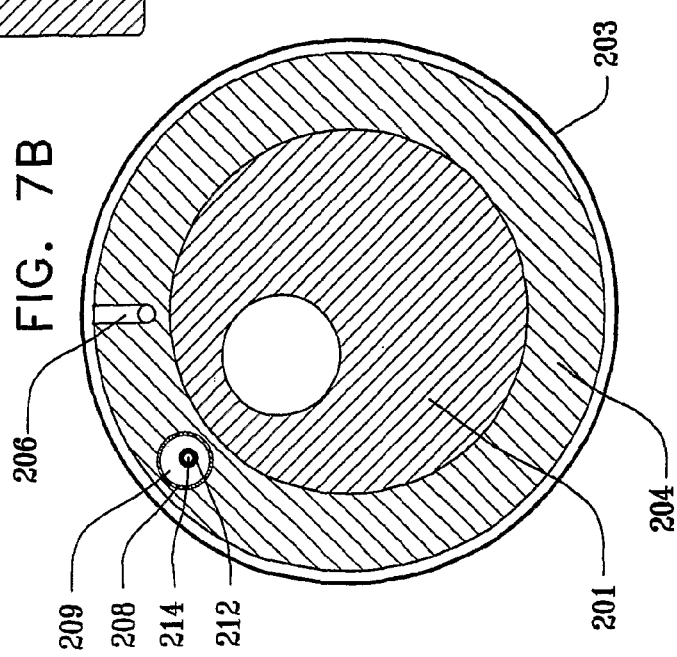

As seen in FIG. 5, the endoscope tool 210 preferably includes a balloon inflation/deflation control interface 222 which communicates with guiding tube 212 at a proximal portion 223 thereof which extends outwardly of a proximal end 224 of external tube 208 and governs inflation and deflation of balloon 216. Additionally, there is preferably provided a peripheral balloon inflation/deflation control interface 225, which communicates with tube 206 and governs inflation and deflation of peripheral balloon 203.

Preferably, the proximal end 224 of external tube 208 is fixed to the proximal portion of endoscope 201 adjacent to an operator control 229 of endoscope 201, by a band 232 or by any other suitable conventional means, such as a clips or medical adhesive tape.

Preferably, the operator positions balloon 216 at a desired location forward of the distal end of endoscope 201 within the generally tubular body portion, by controlled pulling or pushing of the proximal portion 223 of guiding tube 212, relative to the proximal end 224 of external tube 208.

FIG. 8A shows rearward positioning of endoscope tool 210 in which the balloon 216 is located just ahead of the distal end of endoscope 201. The rearward positioning is preferably accomplished by pulling the proximal portion 223 of guiding tube 212 rearwardly relative to the proximal end 224 of external tube 208.

FIG. 8B shows forward positioning of endoscope tool 210 in which the balloon 216 is located a substantial distance forward of the distal end of endoscope 201. The forward positioning is preferably accomplished by pushing the proximal portion 223 of guiding tube 212 forwardly relative to the proximal end 224 of external tube 208.

It is appreciated that controlled positioning of the endoscope tool 210 at desired distances forward of the distal end of endoscope 201 may be achieved by suitable controlled positioning of the proximal portion 223 of guiding tube 212 relative to the proximal end 224 of external tube 208.

It is appreciated that in accordance with a preferred embodiment of the present invention useful for in vivo inspection of a generally tubular body portion having a variable cross-sectional diameter, balloon 216 may be controllably positioned in a range of 0-45 centimeters forward of the distal end of endoscope 201.

Figure 8C:
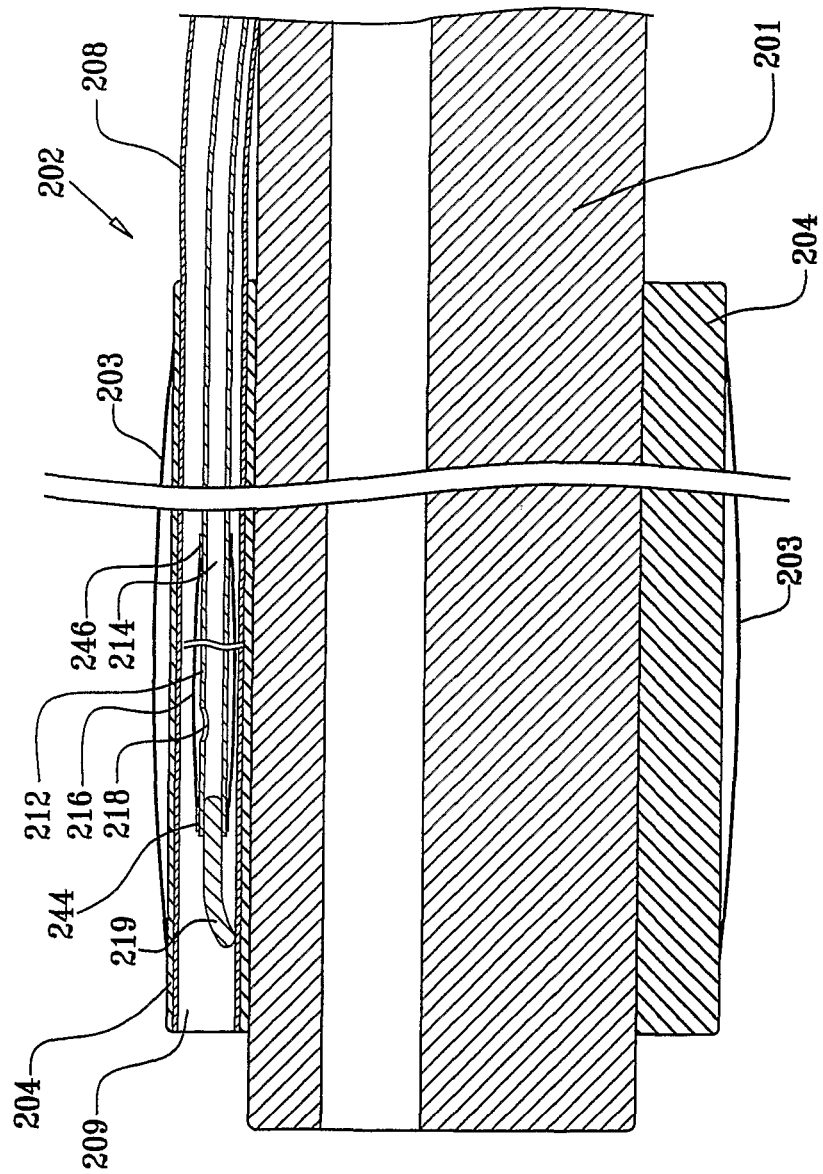

As seen in FIGS. 8A-8D, balloon 216 is fixed to guiding tube 212 via a forward balloon sleeve portion 244 and a rear balloon sleeve portion 246. As seen in FIG. 8C, the cross sectional diameters of balloon 216 in a deflated state and of rear sleeve portion 246 are smaller than the inner cross sectional diameter of external tube 208 and of tubular passageway 209, thereby allowing balloon 216 to be inserted through tubular passageway 209 and through external tube 208. It is appreciated that the distal portion of endoscope tool 210, including balloon 216 and tip portion 219, may be entirely or partially positioned within tubular passageway 209 and external tube 208. It is further appreciated that endoscope tool 210 may be partially or entirely pulled out and be extracted from external tube 208 if applicable. It is yet further appreciated that endoscope tool 210 may be inserted or re-inserted through external tube 208 if applicable, such as for positioning or re-positioning of balloon 216 forward of the distal end of endoscope 201.

Figure 8D:
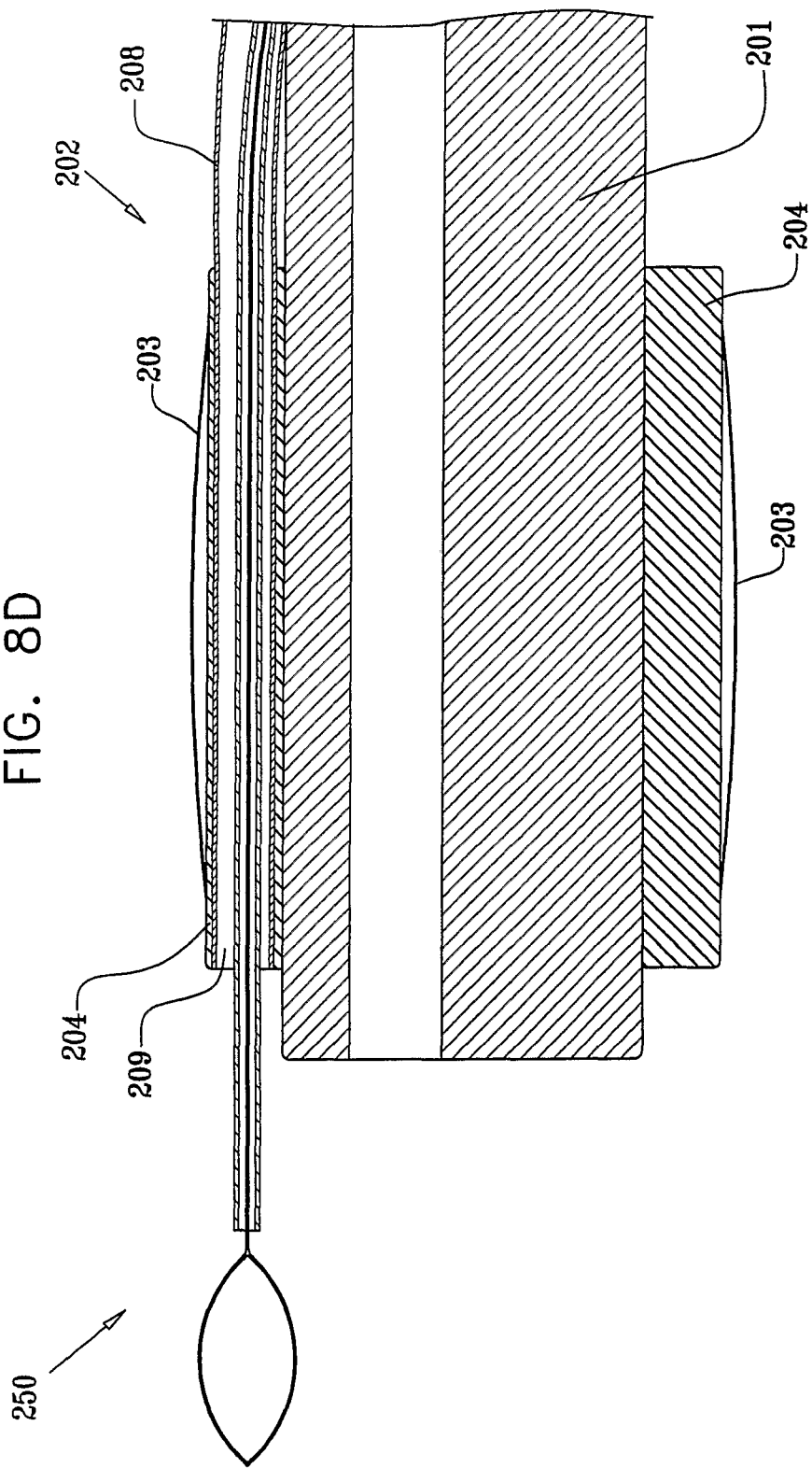

As seen in FIG. 8D, an accessory 250 may be inserted through external tube 208 for medical interaction with a location in the generally tubular body portion forward of the distal end of endoscope 201.

The term "medical interaction" includes for example, inspection, treatment, diagnosis, sampling, removal, marking and any other suitable medical activity.

Accessory 250 may include any conventional accessory such as biopsy forceps, polyp cutter, injection needle, or ultrasound device. It is appreciated that accessory 250 may be inserted instead of or alongside endoscope tool 210. It is further appreciated that accessory 250 may be inserted through an additional external tube (not shown) in case that endoscopy auxiliary assembly 202 comprises more than one external tube 208.

Reference is now made to FIGS. 9-12C, which are respectively a simplified pictorial illustration of an endoscopy system constructed and operative in accordance with a preferred embodiment of the present invention and respective simplified pictorial and sectional view illustrations of an auxiliary assembly constructed and operative in accordance with a preferred embodiment of the present invention.

As seen in FIGS. 9-12C a conventional endoscopy system 300, such as a console including a CV-100 video system center, a CLV-U20 light source, a SONY PVM-2030 video monitor, and an OFP flushing pump, all commercially available from Olympus America Inc. of 2 Corporate Center Drive, Melville, N.Y. 11747, USA, is being employed. The system preferably includes a conventional endoscope 301, which forms part of conventional endoscopy system 300 such as a CIF-100 video enteroscope or a CF-Q160AL video colonoscope which is commercially available from Olympus America Inc. of 2 Corporate Center Drive, Melville, N.Y. 11747, USA.

In accordance with a preferred embodiment of the invention, an endoscopy auxiliary assembly 302 comprising a peripheral balloon 303 may be mounted onto endoscope 301 as shown, by means of a tubular sleeve 304 which is fixed over the distal portion of endoscope 301, and is associated with peripheral balloon 303.

It is appreciated that the tubular sleeve 304 may be constructed of a flexible and stretchable material, such as flexible and stretchable silicon, latex or rubber, thereby enabling it to conform with bending of endoscope 301. It is her appreciated that tubular sleeve 304 may have an untensioned inner diameter slightly smaller than the diameter of endoscope 301, thereby allowing it to be pulled and slid over the endoscope 301 when being stretched, while ensuring firm positioning at the desired location on the distal end of endoscope 301.

Alternatively, tubular sleeve 304 may be constructed of a less stretchable material, such as polyurethane or nylon, and of an inner diameter slightly larger than that of endoscope 301, thereby allowing it to be pulled and slid over the endoscope 301. Preferably tubular sleeve 304 is formed with a relatively thin wall allowing it to be compliant with the bending of endoscope 301. It is appreciated that once positioned at a desired location, tubular sleeve 304 may be fastened to endoscope 301 by any suitable conventional means, such as a medical adhesive tape.

As illustrated in FIGS. 9-12C, peripheral balloon 303 at least partially overlays tubular sleeve 304, and is fixed thereon at both edges by any suitable conventional means such as an adhesive in order to define a sealed volume therebetween. Preferably inflation and deflation of peripheral balloon 303 is provided via a tube 306 communicating with the interior thereof. Tube 306 may be attached to endoscope 301 at multiple locations along its length by any suitable conventional means such as a medical adhesive tape. Alternatively, tube 306 may be detached from endoscope 301.

It is appreciated that in accordance with a preferred embodiment of the present invention peripheral balloon 303 is generally stretchable, and can be inflated to a diameter about 3-10 times larger than its diameter when not inflated. In accordance with a preferred embodiment of the present invention, useful for small intestine endoscopy, the diameter of peripheral balloon 303 when fully inflated is in the range of 3-4 centimeters.

In a specific embodiment, useful for small intestine endoscopy, the diameter of the peripheral balloon when it is fully inflated is four centimeters. Preferably, inflation of the peripheral balloon 303 to a diameter less than four centimeters may be achieved using relatively low pressure, such as in the range of 30-70 millibars.

In another specific embodiment, useful for large intestine endoscopy, the diameter of the peripheral balloon when it is fully inflated is in the range of 4-6 centimeters. In a further embodiment, also useful for large intestine endoscopy, diameter of the peripheral balloon when it is fully inflated is six centimeters. Preferably, inflation of the peripheral balloon 303 to a diameter less than six centimeters may be achieved using relatively low pressure, such as in the range of 30-70 millibars.

It is appreciated that in accordance with a preferred embodiment of the present invention useful for in vivo inspection of a generally tubular body portion having a variable cross-sectional diameter, the expansion diameter range of peripheral balloon 303 is larger than the maximum cross-sectional diameter of the generally tubular body portion, thereby enabling engagement of expanded peripheral balloon 303 with the interior surface of the generally tubular body portion, and anchoring of the endoscope 301 thereto. Preferably, peripheral balloon 303 is a relatively soft, highly compliant balloon, operative to at least partially conform to the shape of the interior surface of the generally tubular body portion when in engagement therewith.

It is appreciated that peripheral balloon 303 may be formed of suitable well-known stretchable materials such as latex, flexible silicon, or highly flexible nylon. Alternatively, peripheral balloon 303 may be formed of polyurethane, which is less stretchable and conforming than latex, flexible silicon or highly flexible nylon. Preferably, the diameter of peripheral balloon 303 is sufficient to ensure tight anchoring at any part of the generally tubular body portion.

In a preferred embodiment of the present invention, endoscopy auxiliary assembly 302 may comprise at least one external tube 308. External tube 308 may be attached to the endoscope 301 at multiple locations along its length by any suitable conventional means such as a medical adhesive tape. Alternatively, external tube 308 may be detached from the endoscope 301.

It is appreciated that external tube 308 may be flexible and highly bendable, allowing it to be compliant with the bending of endoscope 301. It is further appreciated that external tube 308 may be constructed of a low friction material, such as TEFLON®.

In a preferred embodiment of the present invention, external tube 308 may be inserted through a tubular passageway 309 which extends longitudinally within tubular sleeve 304. Alternatively, the tubular passageway may be located interiorly of the sleeve but external to the endoscope 301. External tube 308 may be inserted fully or partially through tubular passageway 309, and may be fixed to tubular sleeve 304 by any conventional means, such as by friction or by use of a suitable adhesive. Alternatively, external tube 308 may be slidable with respect to tubular passageway 309.

An endoscope tool 310, constructed and operative in accordance with a preferred embodiment of the present invention, extends through external tube 308. Endoscope tool 310 preferably comprises a guiding tube 312, which includes at least a first lumen 314 for inflation and deflation of a balloon 316 via an inflation aperture 318. Preferably, the cross-sectional area of guiding tube 312 is sufficiently smaller than that of external tube 308, so as to allow generally free passage of guiding tube 312 through external tube 308, particularly when the external tube 308 is in a bent or curved state, and to allow supply of fluid for inflation or other uses and draining of fluid therethrough.

It is appreciated that guiding tube 312 may be flexible and highly bendable, so as to allow its compliance with the bending of endoscope 301 and with the curves of the intestine. It is further appreciated that guiding tube 312 may be constructed of a low friction material, such as TEFLON®.

Preferably, guiding tube 312 is sealed at its distal end forward of balloon 316 in any suitable manner such as by mechanical sealing or use of an appropriate adhesive, to facilitate inflation and deflation of balloon 316 through guiding tube 312.

Preferably, endoscope tool 310 may comprise a tip portion 319 located distally of balloon 316. The tip portion 319 may be made of a highly flexible tube, such as a TYGON® tube, with a diameter of 1.5 millimeters. The tip portion 319 may be connected to the distal end of guiding tube 312 by any conventional means such as a suitable adhesive. In a preferred embodiment of the present invention the length of tip portion 319 is 20-30 millimeters.

It is appreciated that the high bendability of tip portion 319 prevents endoscope tool 310 from getting stuck in obstacles and bends as it advances through the generally tubular body portion, forward of endoscope 301.

It is appreciated that in accordance with a preferred embodiment of the present invention the endoscope tool 310 and the guiding tube 312 are substantially more flexible than endoscope 301.

It is further appreciated that in accordance with a preferred embodiment of the present invention the tube 306 is generally more flexible than endoscope 301.

It is appreciated that in accordance with yet another preferred embodiment of the present invention the external tube 308 is substantially more flexible than endoscope 301.

It is appreciated that in accordance with a preferred embodiment of the present invention balloon 316 is generally stretchable, and can be inflated to a diameter about 5-20 times larger than its diameter when not inflated. In a specific embodiment, useful for small intestine endoscopy, the balloon diameter when fully inflated is in the range of 3-4 centimeters. In a specific embodiment, useful for small intestine endoscopy, the balloon diameter when fully inflated is four centimeters. Preferably, inflation of the balloon 316 to a diameter less than four centimeters may be achieved using relatively low pressure, such as in the range of 30-70 millibars.

In another preferred embodiment of the present invention, useful for large intestine endoscopy, the balloon diameter when fully inflated is in the range of 4-6 centimeters. In another specific embodiment, useful for large intestine endoscopy, the balloon diameter when fully inflated is six centimeters. Preferably, inflation of the balloon 316 to a diameter less than six centimeters may be achieved using relatively low pressure, such as in the range of 30-70 millibars.

It is appreciated that in accordance with a preferred embodiment of the present invention which is particularly useful for in vivo inspection of a generally tubular body portion having a variable cross-sectional diameter, the expansion range of the diameter of balloon 316 is larger than the maximum cross-sectional diameter of the generally tubular body portion, thereby enabling engagement of expanded balloon 316 with the interior surface of the generally tubular body portion, and anchoring of the endoscope tool 310 thereto. Preferably, balloon 316 is a relatively soft, highly compliant balloon, operative to at least partially conform to the shape of the interior surface of the generally tubular body portion when in engagement therewith.

It is appreciated that balloon 316 may be formed of well-known stretchable materials such as latex, flexible silicon, or highly flexible nylon. Alternatively, balloon 316 may be formed of polyurethane, which is less stretchable and conforming than latex, flexible silicon or highly flexible nylon. Preferably, the diameter of balloon 316 is sufficient to ensure tight anchoring at any location in the generally tubular body portion.

Figure 9:
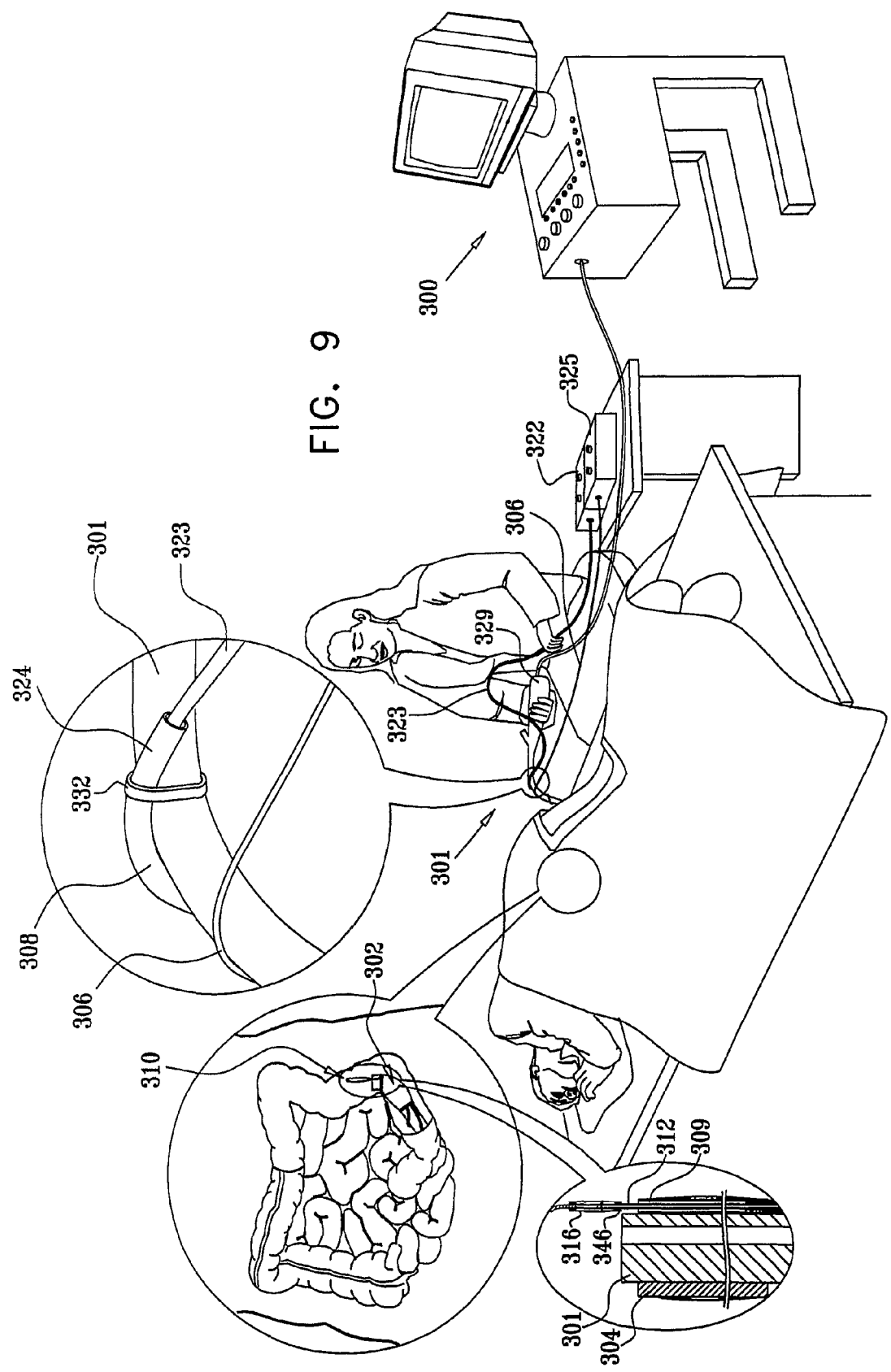
FIG. 9 is a simplified pictorial illustration of an endoscopy system constructed and operative in accordance with yet another preferred embodiment of the present invention.
Figure 10:
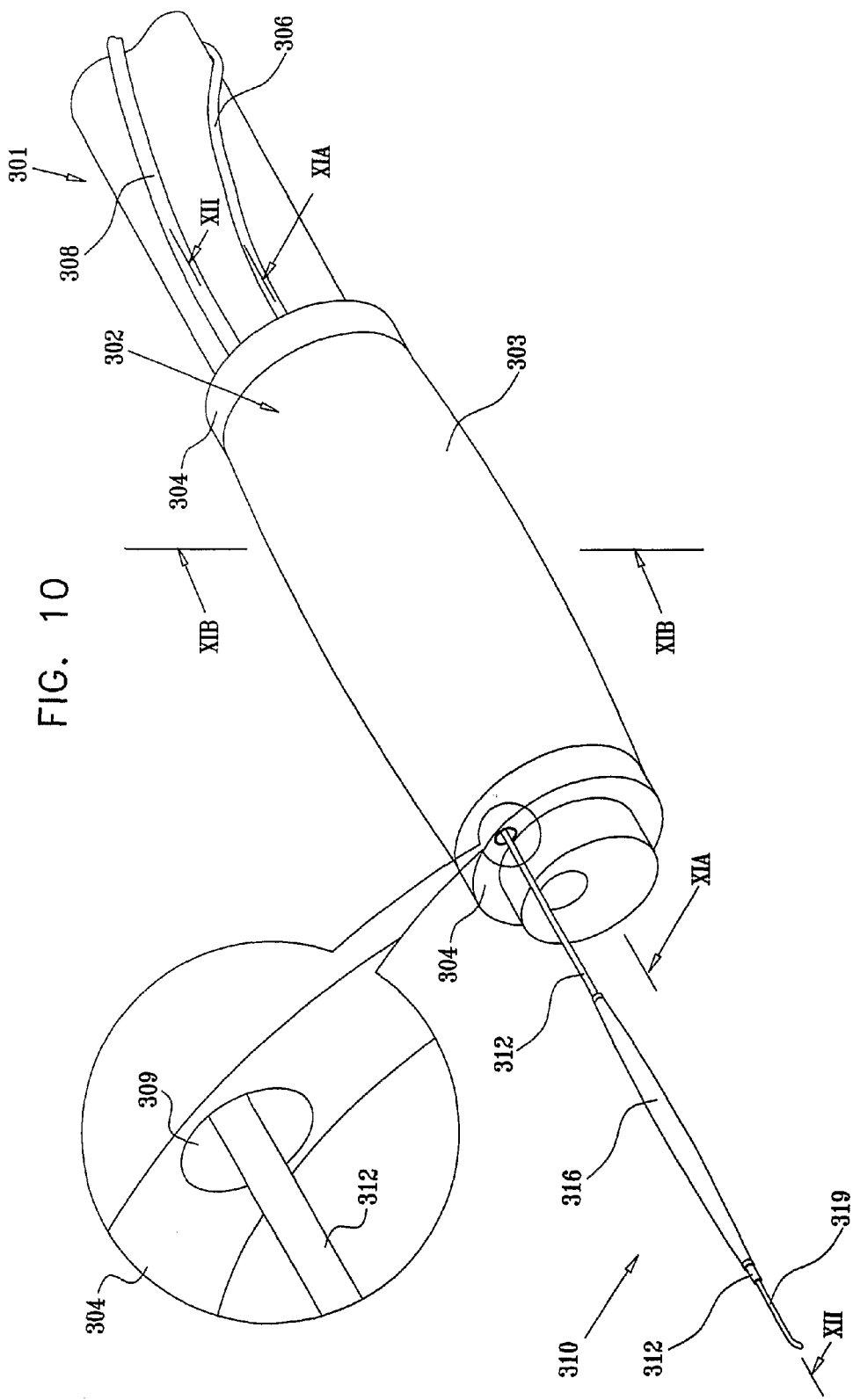
Figure 11A:
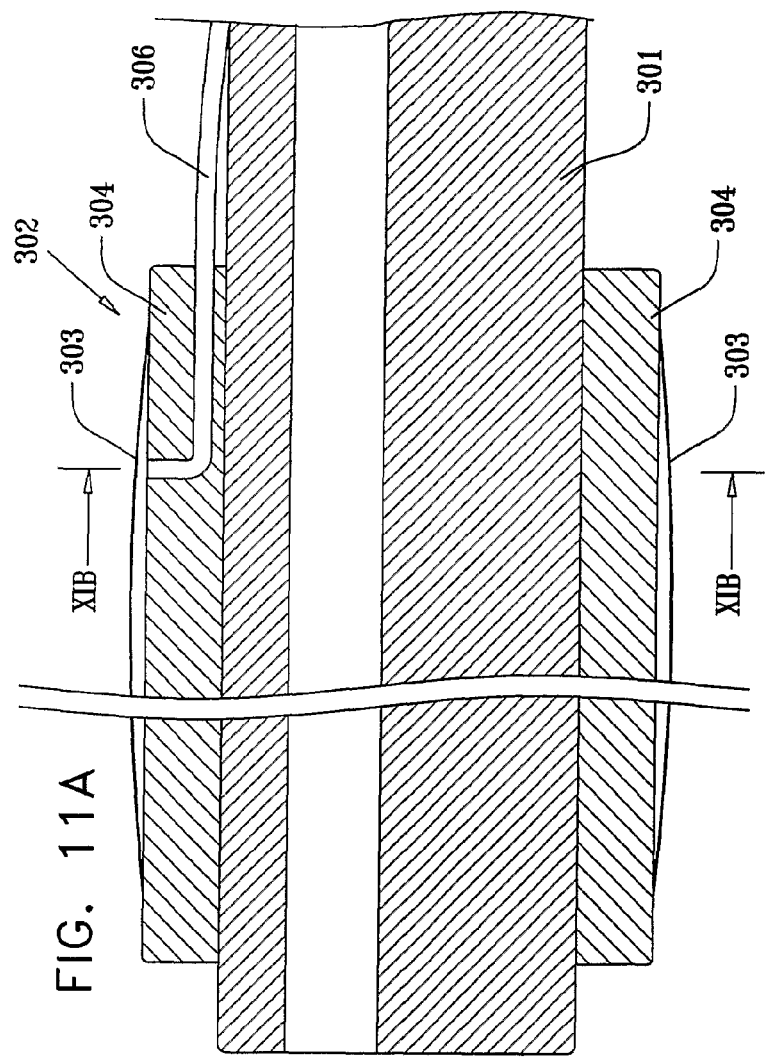
Figure 11B:
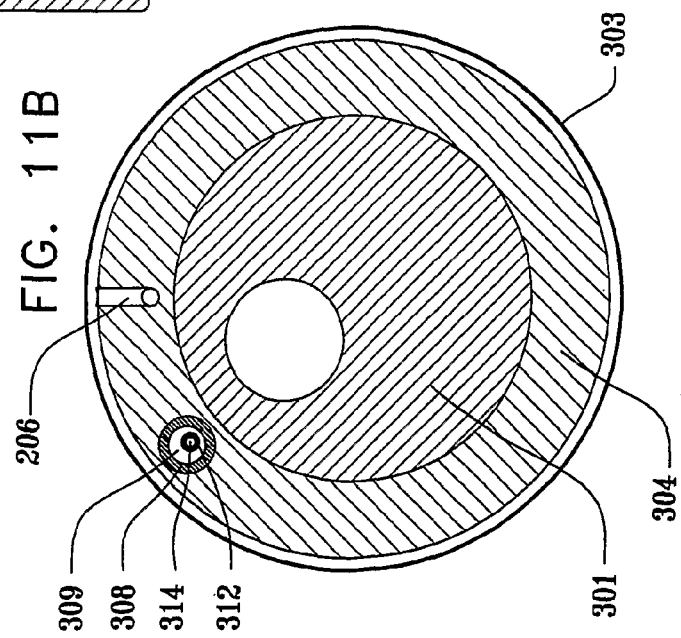

As seen in FIG. 9, the endoscope tool 310 preferably includes a balloon inflation/deflation control interface 322 which communicates with guiding tube 312 at a proximal portion 323 thereof which extends outwardly of a proximal end 324 of external tube 308 and governs inflation and deflation of balloon 316. Additionally, there is preferably provided a peripheral balloon inflation/deflation control interface 325, which communicates with tube 306 and governs inflation and deflation of peripheral balloon 303.

Preferably, proximal end 324 of external tube 308 is fixed to the proximal portion of endoscope 301 adjacent to an operator control 329 of endoscope 301, by a band 332 or by any other suitable conventional means, such as a clips or medical adhesive tape.

Preferably, the operator positions balloon 316 at a desired location forward of the distal end of endoscope 301 within the generally tubular body portion, by controlled pulling or pushing of the proximal portion 323 of guiding tube 312, relative to the proximal end 324 of external tube 308.

FIG. 12A shows rearward positioning of endoscope tool 310 in which the balloon 316 is located just ahead of the distal end of endoscope 301. The rearward positioning is preferably accomplished by pulling the proximal portion 323 of guiding tube 312 rearwardly relative to the proximal end 324 of external tube 308.

Figure 12B:
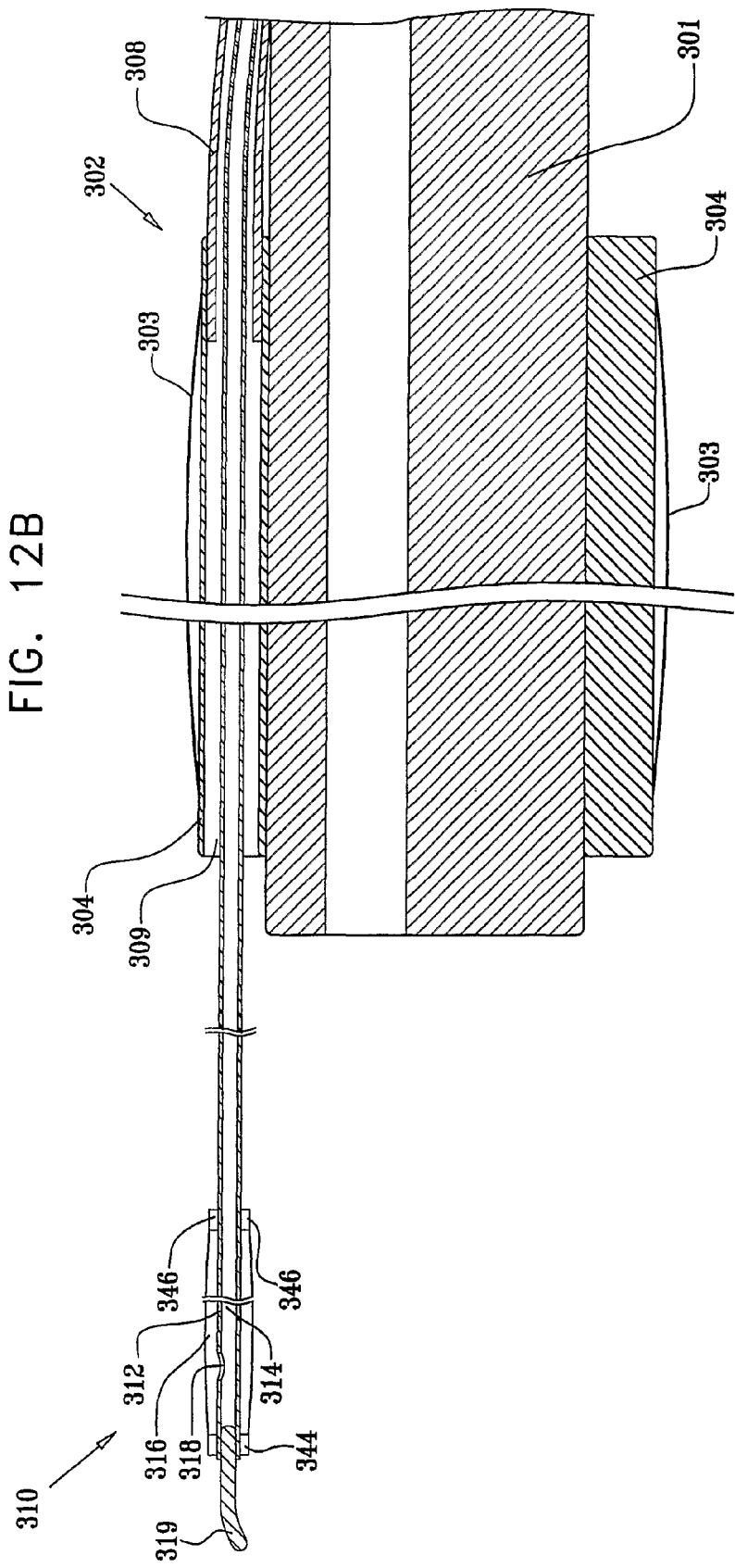

FIG. 12B shows forward positioning of endoscope tool 310 in which the balloon 316 is located a substantial distance forward of the distal end of endoscope 301. The forward positioning is preferably accomplished by pushing the proximal portion 323 of guiding tube 312 forwardly relative to the proximal end 324 of external tube 308.

It is appreciated that controlled positioning of the endoscope tool 310 at desired distances forward of the distal end of endoscope 301 may be achieved by suitable controlled positioning of the proximal portion 323 of guiding tube 312 relative to the proximal end 324 of external tube 308.

It is appreciated that in accordance with a preferred embodiment of the present invention useful for in vivo inspection of a generally tubular body portion having a variable cross-sectional diameter, balloon 316 may be controllably positioned in a range of 0-45 centimeters forward of the distal end of endoscope 301.

Figure 12C:
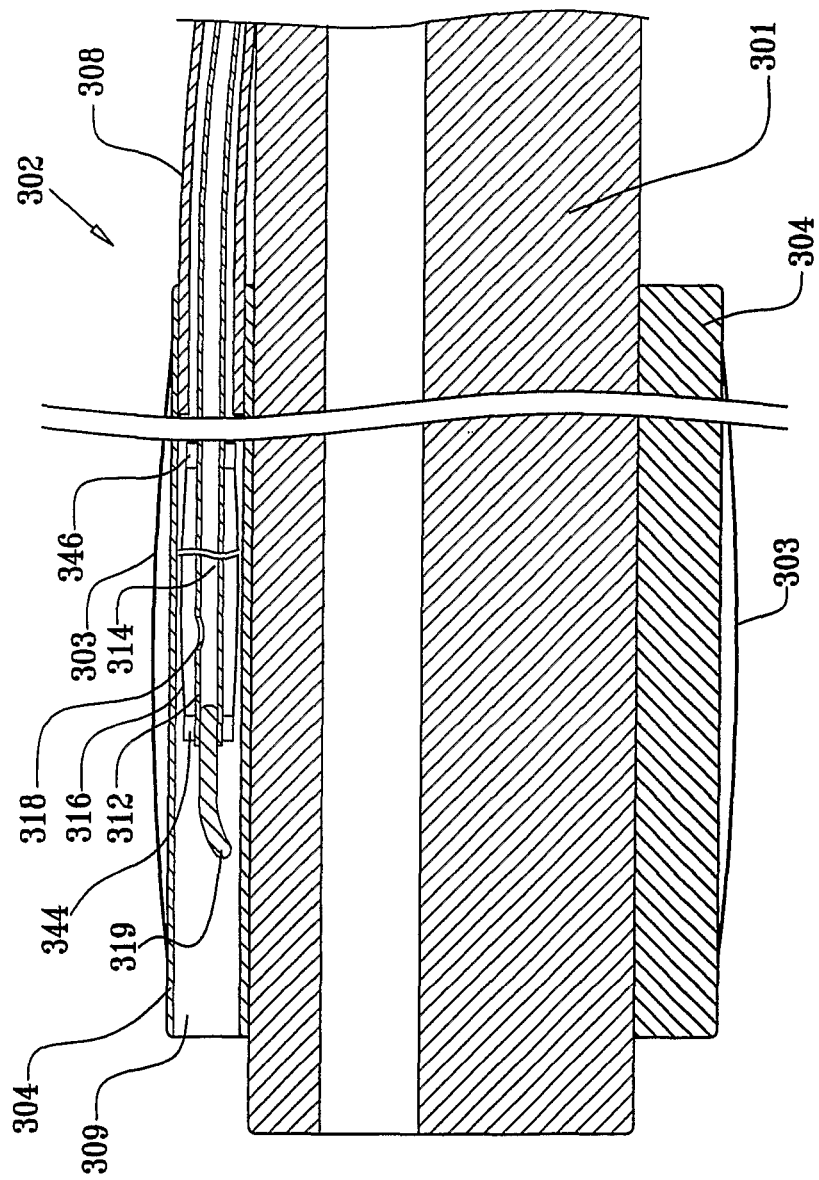

As seen in FIGS. 12A-12C, balloon 316 is fixed to guiding tube 312 via a forward balloon sleeve portion 344 and a rear balloon sleeve portion 346. As seen in FIG. 12C, the cross sectional diameter of rear sleeve portion 346 is larger than the inner cross sectional diameter of external tube 308, thereby preventing balloon 316 from being inserted through external tube 308. As further seen in FIG. 12C, the cross sectional diameters of balloon 316 in a deflated state and of rear sleeve portion 346 are smaller than the inner cross sectional diameter of tubular passageway 309, thereby allowing balloon 316 to be inserted through tubular passageway 309. It is appreciated that the distal portion of endoscope tool 310, including balloon 316 and tip portion 319, may be entirely or partially positioned within tubular passageway 309.

It is appreciated that rear sleeve portion 346 may function as a stopper that prevents further pulling of guiding tube 312 when rear sleeve portion 346 is in contact with external tube 308, inside tubular sleeve 309.

Reference is now made to FIGS. 13-16B, which are respectively a simplified pictorial illustration of an endoscopy system constructed and operative in accordance with a preferred embodiment of the present invention and respective simplified pictorial and sectional view illustrations of an auxiliary assembly constructed and operative in accordance with a preferred embodiment of the present invention.

As seen in FIGS. 13-16B a conventional endoscopy system 400, such as a console including a CV-100 video system center, a CLV-U20 light source, a SONY PVM-2030 video monitor, and an OFP flushing pump, all commercially available from Olympus America Inc. of 2 Corporate Center Drive, Melville, N.Y. 11747, USA, is being employed. The system preferably includes a conventional endoscope 401, which forms part of conventional endoscopy system 400, such as a CIF-100 video enteroscope or a CF-Q160AL video colonoscope which is commercially available from Olympus America Inc. of 2 Corporate Center Drive, Melville, N.Y. 11747, USA.

In accordance with a preferred embodiment of the invention, an endoscopy auxiliary assembly 402 comprising a peripheral balloon 403 may be mounted onto endoscope 401 as shown, by means of a tubular sleeve 404 which is fixed over the distal portion of endoscope 401, and is associated with peripheral balloon 403. It is appreciated that the tubular sleeve 404 may be constructed of a flexible and stretchable material, such as flexible and stretchable silicon, latex or rubber, thereby enabling it to conform with bending of endoscope 401. It is further appreciated that tubular sleeve 404 may have an untensioned inner diameter slightly smaller than the diameter of endoscope 401, thereby allowing it to be pulled and slid over the endoscope 401 when being stretched, while ensuring firm positioning at the desired location on the distal end of endoscope 401.

Alternatively, tubular sleeve 404 may be constructed of a less stretchable material, such as polyurethane or nylon, and of an inner diameter slightly larger than that of endoscope 401, thereby allowing it to be pulled and slid over endoscope 401. Preferably tubular sleeve 404 is formed with a relatively thin wall allowing it to be compliant with the bending of endoscope 401. It is appreciated that once positioned at a desired location, tubular sleeve 404 may be fastened to endoscope 401 by any suitable conventional means, such as a medical adhesive tape.

As illustrated in FIGS. 13-16B, peripheral balloon 403 at least partially overlays tubular sleeve 404, and is fixed thereon at both edges by any suitable conventional means such as an adhesive in order to define a sealed volume therebetween. Preferably inflation and deflation of peripheral balloon 403 is provided via a tube 406 communicating with the interior thereof. Tube 406 may be attached to endoscope 401 at multiple locations along its length by any suitable conventional means such as a medical adhesive tape. Alternatively, tube 406 may be detached from endoscope 401.

It is appreciated that in accordance with a preferred embodiment of the present invention peripheral balloon 403 is generally stretchable, and can be inflated to a diameter about 3-10 times larger than its diameter when not inflated. In accordance with a preferred embodiment of the present invention, useful for small intestine endoscopy, the diameter of peripheral balloon 403 when fully inflated is in the range of 3-4 centimeters.

In a specific embodiment, useful for small intestine endoscopy, the diameter of the peripheral balloon diameter when it is fully inflated is four centimeters. Preferably, inflation of the peripheral balloon 403 to a diameter less than four centimeters may be achieved using relatively low pressure, such as in the range of 30-70 millibars.

In another specific embodiment, useful for large intestine endoscopy, the diameter of the peripheral balloon when it is fully inflated is in the range of 4-6 centimeters. In a further embodiment, also useful for large intestine endoscopy, diameter of the peripheral balloon when it is fully inflated is six centimeters. Preferably, inflation of the peripheral balloon 403 to a diameter less than six centimeters may be achieved using relatively low pressure, such as in the range of 30-70 millibars.

It is appreciated that in accordance with a preferred embodiment of the present invention useful for in vivo inspection of a generally tubular body portion having a variable cross-sectional diameter, the expansion diameter range of peripheral balloon 403 is larger than the maximum cross-sectional diameter of the generally tubular body portion, thereby enabling engagement of expanded peripheral balloon 403 with the interior surface of the generally tubular body portion, and anchoring of the endoscope 401 thereto. Preferably, peripheral balloon 403 is a relatively soft, highly compliant balloon, operative to at least partially conform to the shape of the interior surface of the generally tubular body portion when in engagement therewith.

It is appreciated that peripheral balloon 403 may be formed of suitable well-known stretchable materials such as latex, flexible silicon, or highly flexible nylon. Alternatively, peripheral balloon 403 may be formed of polyurethane, which is less stretchable and conforming than latex, flexible silicon or highly flexible nylon. Preferably, the diameter of peripheral balloon 403 is sufficient to ensure tight anchoring at any part of the generally tubular body portion.

In a preferred embodiment of the present invention, endoscopy auxiliary assembly 402 may comprise at least one external tube 408. External tube 408 may be attached to the endoscope 401 at multiple locations along its length by any suitable conventional means such as a medical adhesive tape. Alternatively, external tube 408 may be detached from the endoscope 401.

It is appreciated that external tube 408 may be flexible and highly bendable, allowing it be compliant with the bending of endoscope 401. It is further appreciated that external tube 408 may be constructed of a low friction material, such as TEFLON®.

In a preferred embodiment of the present invention, external tube 408 may be inserted through a tubular passageway 409 which extends longitudinally within tubular sleeve 404. Alternatively, the tubular passageway may be located interiorly of the sleeve but external to the endoscope 401. External tube 408 may be inserted fully or partially through tubular passageway 409 and may be fixed to tubular sleeve 404 by any conventional means, such as by friction or by use of a suitable adhesive. Alternatively, external tube 408 may be slidable with respect to tubular passageway 409.

An endoscope tool 410, constructed and operative in accordance with a preferred embodiment of the present invention extends through the external tube 408. Endoscope tool 410 preferably comprises a guiding tube 412, which includes at least a first lumen 414 for inflation and deflation of a balloon 416 via an inflation aperture 418. Preferably, the cross-sectional area of guiding tube 412 is sufficiently smaller than that of external tube 408, so as to allow generally free passage of guiding tube 412 through external tube 408, particularly when the external tube 408 is in a bent or curved state, and to allow supply of fluid for inflation or other uses and draining of fluid therethrough.

Preferably, a plurality of short hollow cylinders 420 may be disposed longitudinally within tubular passageway 409, as shown in FIGS. 16A and 16B. Adjacent hollow cylinders 420 may be separated by spaces 421.

It is appreciated that hollow cylinders 420 may be relatively flexible and bendable, so as to comply with the bending of endoscope 401 and of tubular sleeve 404. Alternatively, hollow cylinders 420 may be relatively rigid. It is appreciated that hollow cylinders 420 may be constructed of a low friction material, such as TEFLON®.

Preferably, hollow cylinders 420 lead guiding tube 412 within tubular passageway 409 and allow smooth and low friction passage of guiding tube 412.

It is appreciated that hollow cylinders 420 support the inner walls of tubular passageway 409 and prevent the collapse of the inner walls of tubular passageway 409 towards guiding tube 412, especially in a bent state of endoscope 401 and tubular sleeve 404.

In accordance with a preferred embodiment of the present invention, the length of hollow tubes 420 may be in the range of 5-25 millimeters, and the length of spaces 421 may be in the range of 2-10 millimeters.

It is appreciated that guiding tube 412 may be flexible and highly bendable, so as to allow its compliance with the bending of endoscope 401 and with the curves of the intestine. It is further appreciated that guiding tube 412 may be constructed of a low friction material, such as TEFLON®.

Preferably, guiding tube 412 is sealed at its distal end forward of balloon 416 in any suitable manner such as by mechanical sealing or use of an appropriate adhesive, to facilitate inflation and deflation of balloon 416 through guiding tube 412.

Preferably, endoscope tool 410 comprises a tip portion 419 located distally of balloon 416. The tip portion 419 may be made of a highly flexible tube, such as a TYGON® tube with a diameter of 1.5 millimeters. The tip portion 419 may be connected to the distal end of guiding tube 412 by any conventional means such as a suitable adhesive. In a preferred embodiment of the present invention the length of tip portion 419 is 20-30 millimeters.

It is appreciated that the high bendability of tip portion 419 prevents endoscope tool 410 from getting stuck in obstacles and bends as it advances through the generally tubular body portion, forward of endoscope 401.

It is appreciated that in accordance with a preferred embodiment of the present invention the endoscope tool 410 and the guiding tube 412 are substantially more flexible than endoscope 401.

It is further appreciated that in accordance with a preferred embodiment of the present invention the tube 406 is substantially more flexible than endoscope 401.

It is appreciated that in accordance with yet another preferred embodiment of the present invention the external tube 408 is substantially more flexible than endoscope 401.

It is appreciated that in accordance with a preferred embodiment of the present invention balloon 416 is generally stretchable, and can be inflated to a diameter about 5-20 times larger than its diameter when not inflated. In a specific embodiment, useful for small intestine endoscopy, the balloon diameter when fully inflated is in the range of 3-4 centimeters. In a specific embodiment, useful for small intestine endoscopy, the balloon diameter when fully inflated is four centimeters. Preferably, inflation of the balloon 416 to a diameter less than four centimeters may be achieved using relatively low pressure, such as in the range of 30-70 millibars.

In another preferred embodiment of the present invention, useful for large intestine endoscopy, the balloon diameter when fully inflated is in the range of 4-6 centimeters. In another specific embodiment, useful for large intestine endoscopy, the balloon diameter when fully inflated is six centimeters. Preferably, inflation of the balloon 416 to a diameter less than six centimeters may be achieved using relatively low pressure, such as in the range of 30-70 millibars.

It is appreciated that in accordance with a preferred embodiment of the present invention which is particularly useful for in vivo inspection of a generally tubular body portion having a variable cross-sectional diameter, the expansion range of the diameter of balloon 416 is larger than the maximum cross-sectional diameter of the generally tubular body portion, thereby enabling engagement of expanded balloon 416 with the interior surface of the generally tubular body portion, and anchoring of the endoscope tool 410 thereto. Preferably, balloon 416 is a relatively soft, highly compliant balloon, operative to at least partially conform to the shape of the interior surface of the generally tubular body portion when in engagement therewith.

It is appreciated that balloon 416 may be formed of well-known stretchable materials such as latex, flexible silicon, or highly flexible nylon. Alternatively, balloon 416 may be formed of polyurethane, which is less stretchable and conforming than latex, flexible silicon or highly flexible nylon. Preferably, the diameter of balloon 416 is sufficient to ensure tight anchoring at any location of the generally tubular body portion.

Figure 13:
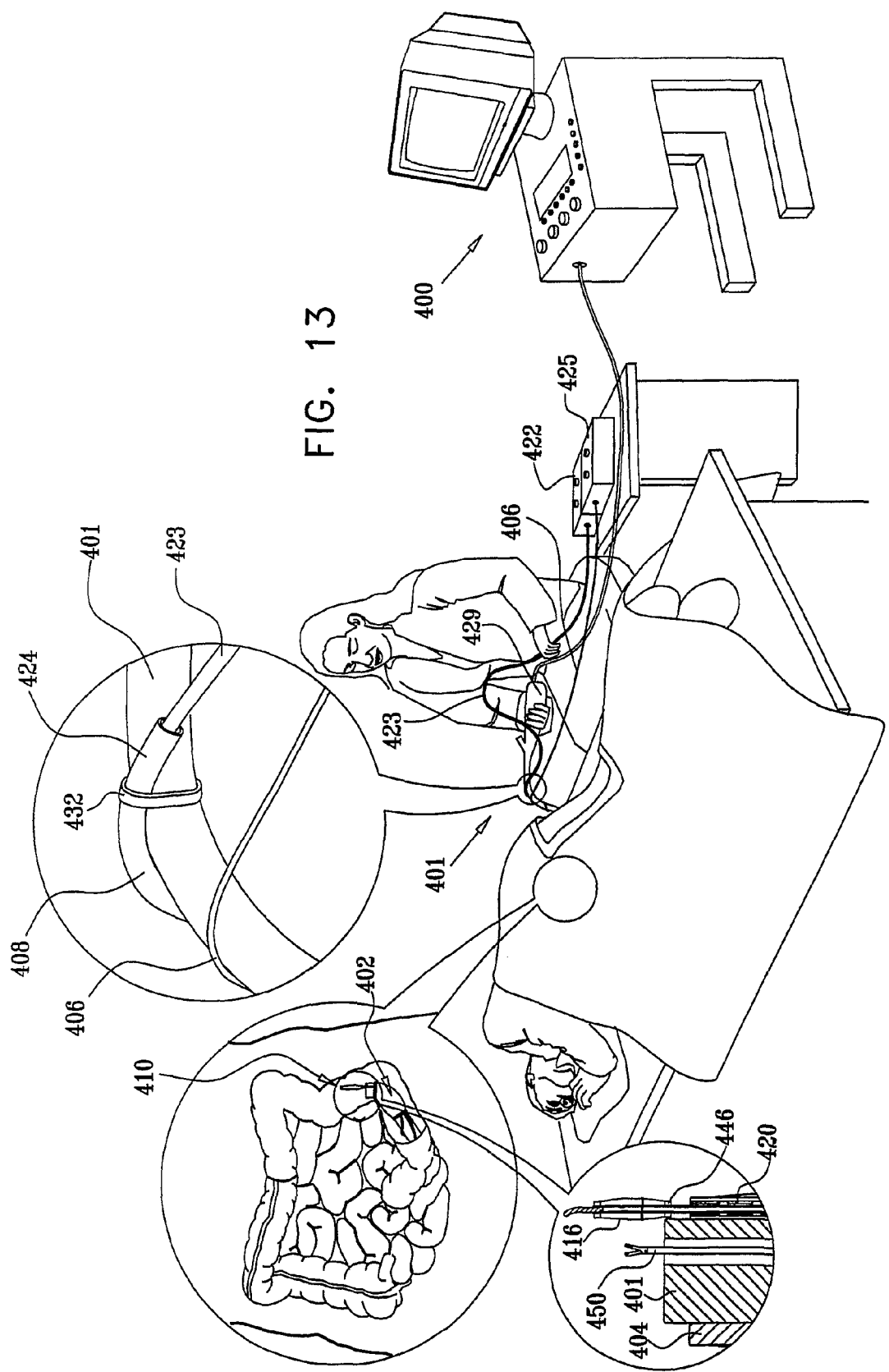
FIG. 13 is a simplified pictorial illustration of an endoscopy system constructed and operative in accordance with further another preferred embodiment of the present invention.
Figure 14:
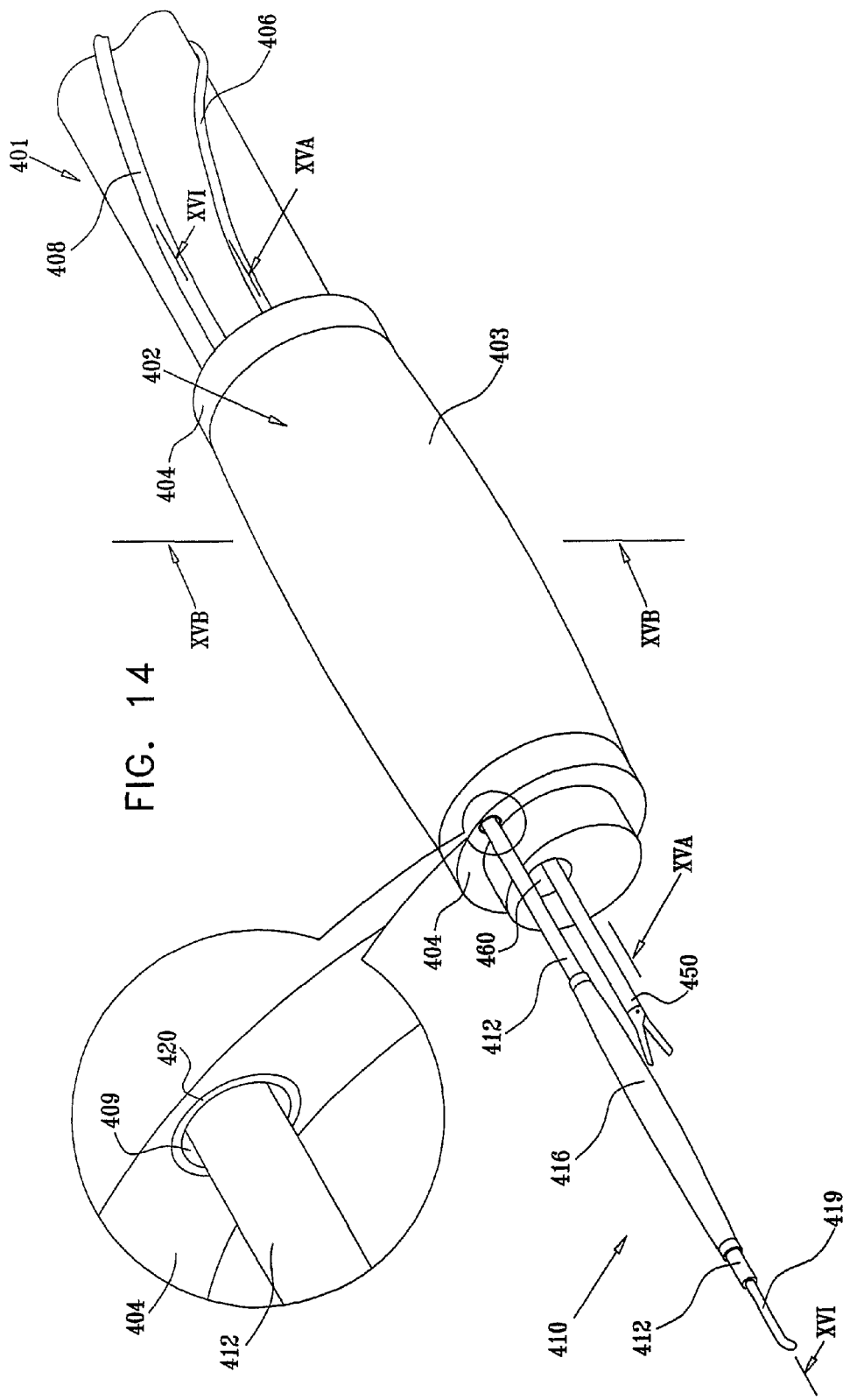

As seen in FIG. 13, the endoscope tool 410 preferably includes a balloon inflation/deflation control interface 422 which communicates with guiding tube 412 at a proximal portion 423 thereof which extends outwardly of a proximal end 424 of external tube 408 and governs inflation and deflation of balloon 416. Additionally, there is preferably provided a peripheral balloon inflation/deflation control interface 425, which communicates with tube 406 and governs inflation and deflation of peripheral balloon 403.

Preferably, proximal end 424 of external tube 408 is fixed to the proximal portion of endoscope 401 adjacent to an operator control 429 of endoscope 401, by a band 432 or by any other suitable conventional means, such as a clips or medical adhesive tape.

Preferably, the operator positions balloon 416 at a desired location forward of the distal end of endoscope 401 within the generally tubular body portion, by controlled pulling or pushing of the proximal portion 423 of guiding tube 412, relative to the proximal end 424 of external tube 408.

FIG. 16A shows rearward positioning of endoscope tool 410 in which the balloon 416 is located just ahead of the distal end of endoscope 401. The rearward positioning is preferably accomplished by pulling the proximal portion 423 of guiding tube 412 rearwardly relative to the proximal end 424 of external tube 408.

FIG. 16B shows forward positioning of endoscope tool 410 in which the balloon 416 is located a substantial distance forward of the distal end of endoscope 401. The forward positioning is preferably accomplished by pushing the proximal portion 423 of guiding tube 412 forwardly relative to the proximal end 424 of external tube 408.

It is appreciated that controlled positioning of the endoscope tool 410 at desired distances forward of the distal end of endoscope 401 may be achieved by suitable controlled positioning of the proximal portion 423 of guiding tube 412 relative to the proximal end 424 of external tube 408.

It is appreciated that in accordance with a preferred embodiment of the present invention useful for in vivo inspection of a generally tubular body portion having a variable cross-sectional diameter, balloon 416 may be controllably positioned in a range of 0-45 centimeters forward of the distal end of endoscope 401.

As seen in FIGS. 16A and 16B, balloon 416 is fixed to guiding tube 412 via a forward balloon sleeve portion 444 and a rear balloon sleeve portion 446. As seen in FIG. 16A, the cross sectional diameter of rear sleeve portion 446 is larger than the inner cross sectional diameter of external tube 408 and larger than the inner cross sectional diameter of tubular passageway 409, thereby preventing balloon 416 from being inserted through external tube 408 and through tubular passageway 409.

It is appreciated that rear sleeve portion 446 may function as a stopper that prevents further pulling of guiding tube 412 when rear sleeve portion 446 is in contact with tubular sleeve 404 or with external tube 408.

In accordance with a preferred embodiment of the present invention useful for in vivo inspection of a generally tubular body portion, an additional accessory 450 may be inserted through an instrument channel 460 of endoscope 401 for medical interaction with the generally tubular body portion at a location forward of the distal end of endoscope 401. Accessory 450 may incorporate any conventional accessory such as biopsy forceps, polyp cutter, injection needle, or ultrasound device.

It is appreciated that accessory 450 may be provided instead of or in addition to endoscope tool 410. Accessory 450 may be operative within the generally tubular body portion at the same time or alternating with the operation of endoscopy auxiliary assembly 402 and endoscope tool 410.

Reference is now made to FIGS. 17A, 17B, 17C, 17D, 17E, 17F, 17G, 17H, 17I and 17J, which are simplified illustrations of the endoscopy auxiliary assembly 402 and endoscope tool 410 of FIGS. 13-16B in various operative orientations within an intestine. In the illustrated embodiment, desired orientation of the forward end of the endoscope tool 410 is obtained by suitable axial displacement of the tool through the external tube 408 of endoscopy auxiliary assembly 402.

Figure 17A:
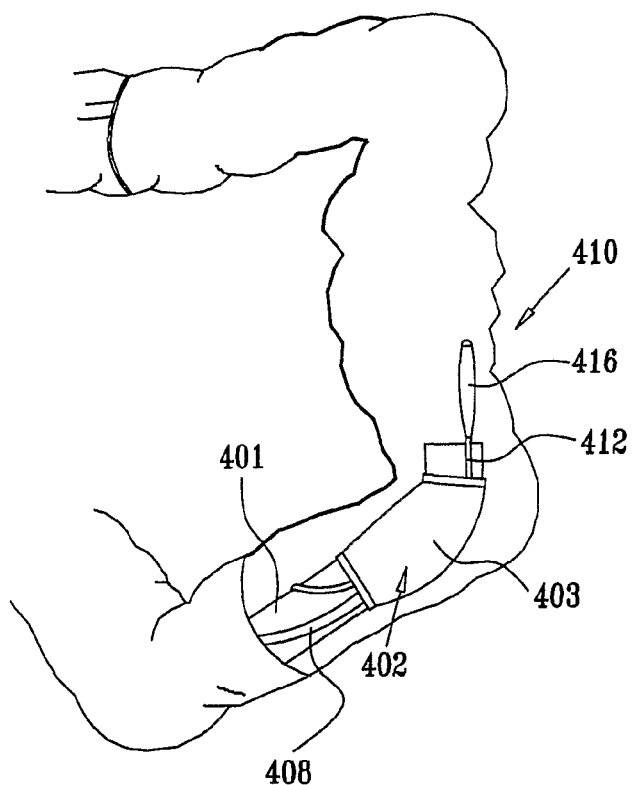
FIGS. 17A, 17B, 17C, 17D, 17E, 17F, 17G, 17H, 17I and 17J are simplified illustrations of various functionalities which may be provided by the systems of FIGS. 13-16B.

As seen in FIG. 17A, endoscope tool 410 is located adjacent the distal end of the endoscope 401, and balloon 416, in a deflated state, protrudes a short distance forward of the distal end of endoscope 401. As seen, peripheral balloon 403 is in a deflated state.

Figure 17B:
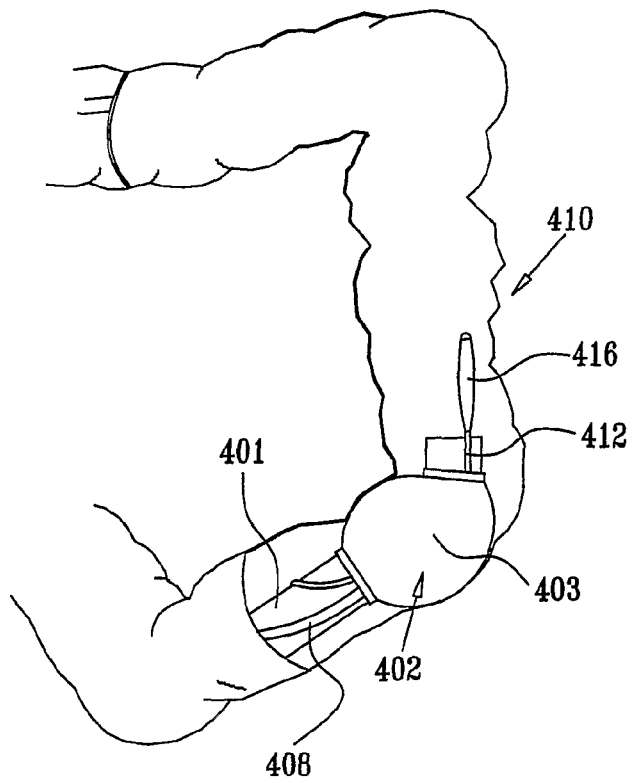

FIG. 17B shows peripheral balloon 403 in an inflated state in engagement with an interior wall of the intestine, thereby anchoring the endoscope 401 thereat.

Figure 17C:
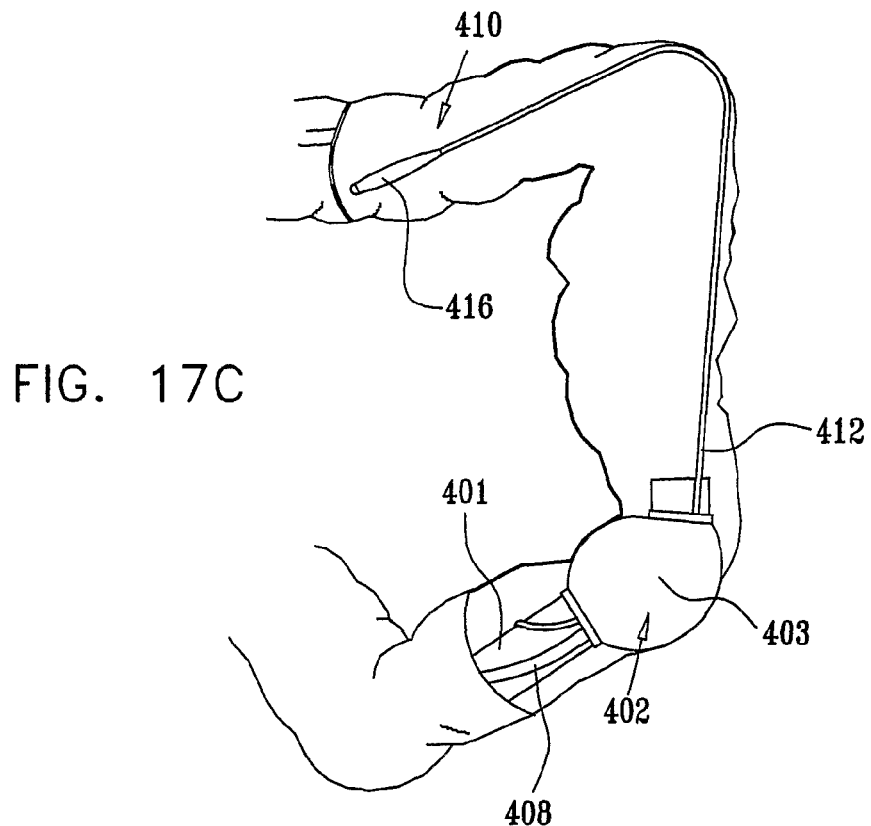

FIG. 17C shows forward progress of the endoscope tool 410 through the intestine resulting from pushing of the tool forward relative to the endoscope in a conventional manner.

Figure 17D:
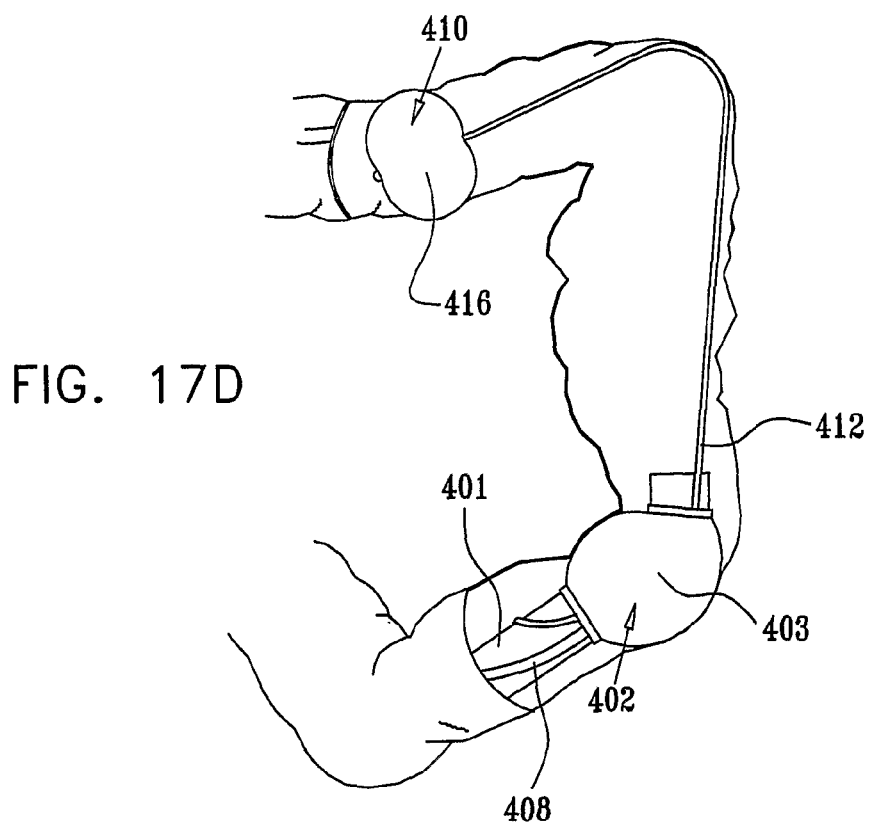

FIG. 17D shows inflation of the balloon 416. In accordance with a preferred embodiment of the invention, this inflation anchors the forward end of the endoscope tool 410 to the intestine at the location of the balloon 416.

Figure 17E:
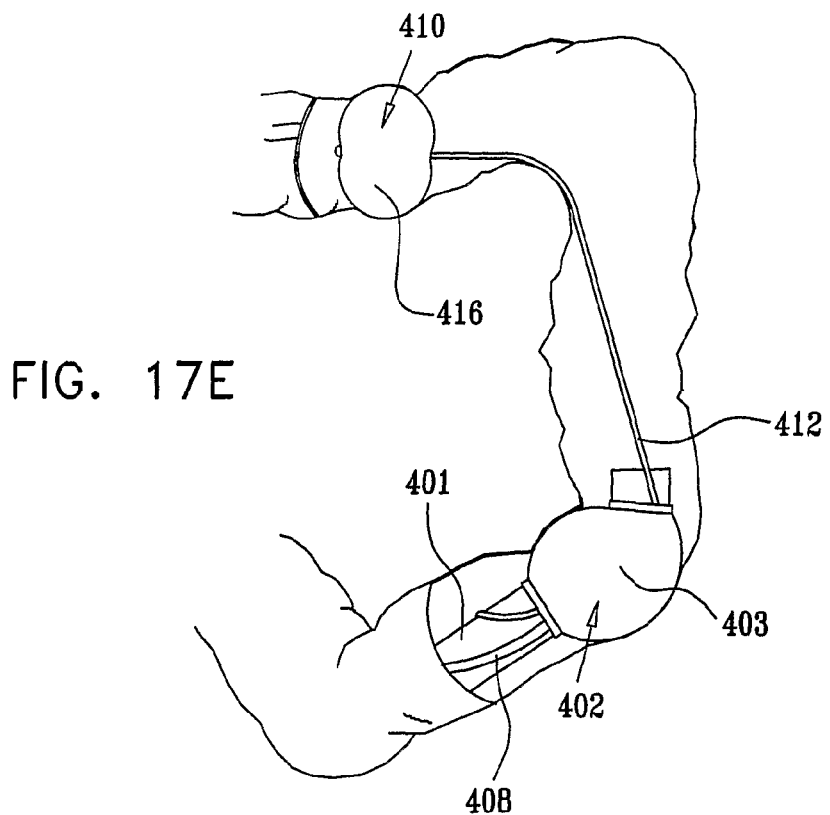

FIG. 17E shows tensioning the guiding tube 412 of the endoscope tool 410 by pulling on the guiding tube 412.

Figure 17F:
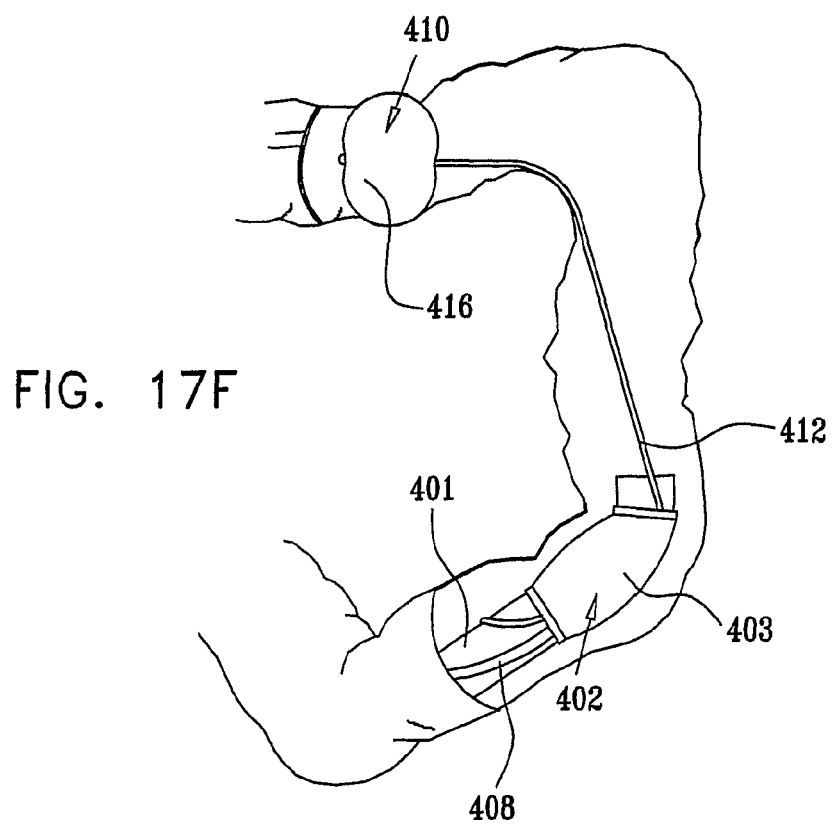

FIG. 17F shows deflation of peripheral balloon 403.

Figure 17G:
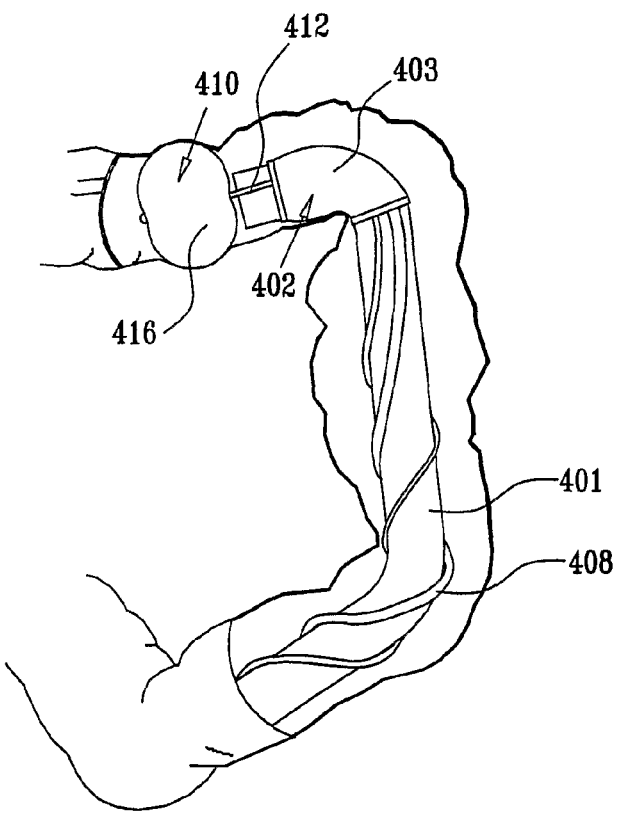

FIG. 17G shows the endoscope 401 having been pushed forward along the guiding tube 412, using the guiding tube 412 as a guide wire in a conventional manner. Alternatively to pushing endoscope 401 or in parallel to pushing endoscope 401, endoscope tool 410 may be pulled by pulling on the guiding tube 412 while balloon 416 is in an inflated state and thereby anchored to the intestine.

Figure 17H:
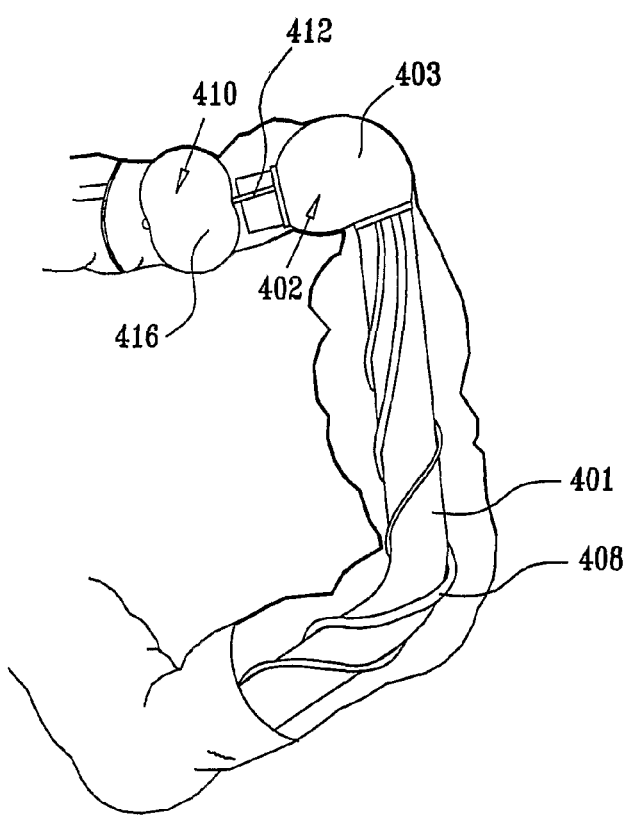

FIG. 17H shows inflation of peripheral balloon 403 into engagement with an interior wall of the intestine, thereby anchoring the endoscope 401 thereat.

Figure 17I:
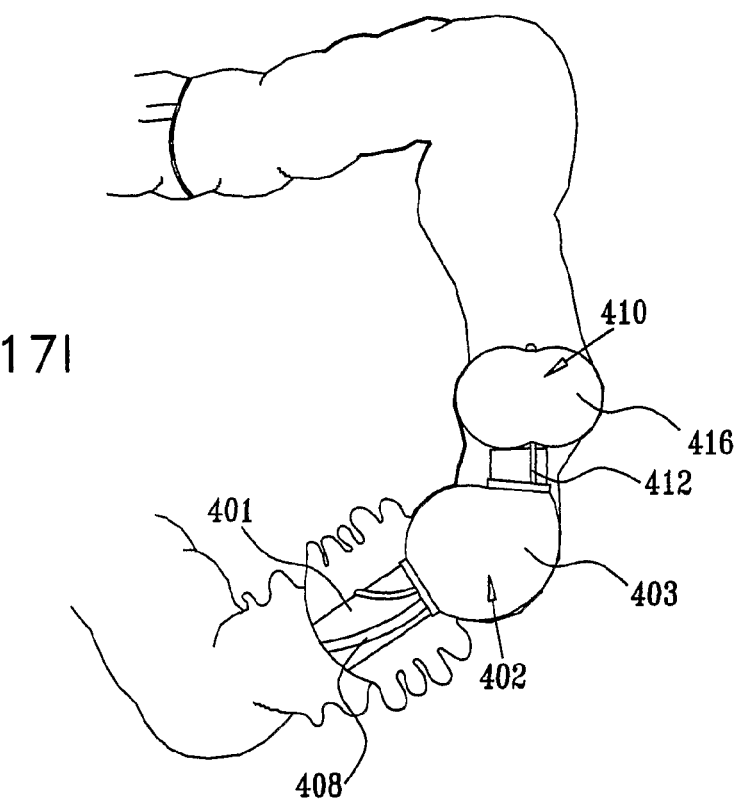

Thereafter, as shown in FIG. 17I, the endoscope 401 and the endoscope tool 410 may be pulled together, while anchored to interior walls of the intestine. This pulling action may bunch together a portion of the intestine over part of the endoscope 401, as shown.

Figure 17J:
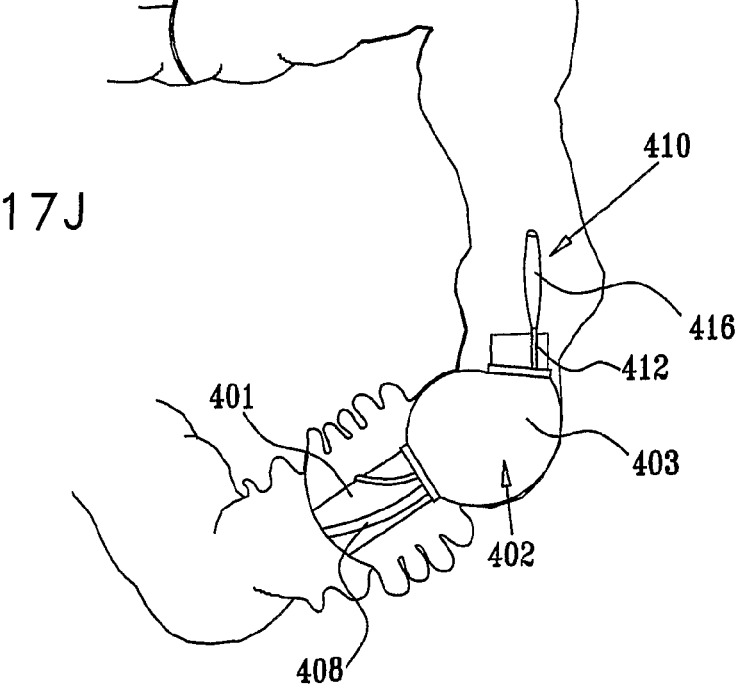

Thereafter, as shown in FIG. 17J, the balloon 416 may be deflated.

Further forward progress of the endoscope through the intestine, preferably to a position where the distal end of endoscope 401 lies just behind the balloon 416, similarly to the orientation shown in FIG. 17B, may be achieved by repeating some or all of the steps described hereinabove with reference to FIGS. 17B-17J, as required by the geometries encountered.

Similarly, backward progress of the endoscope through the intestine may be achieved by repeating some or all of the steps described hereinabove with reference to FIGS. 17B-17J in a different order and preferably in a reversed order, as required by the geometries encountered.

It is appreciated that air for inflation may be supplied to the interior of the intestine intermediate peripheral balloon 403 and balloon 416 in some or all of the operative orientations which are described hereinabove, corresponding to FIGS. 17A-17J. Specifically, air for inflation may be supplied to the interior of the intestine intermediate peripheral balloon 403 and balloon 416 in operative orientations corresponding to FIGS. 17D, 17E, 17H and 17I, in which the intestine is generally sealed intermediate the two inflated balloons. Air for inflation may be supplied to the interior of the intestine intermediate peripheral balloon 403 and balloon 416 in operative orientations corresponding to FIGS. 17B, 17C, 17F, 17G and 17J, in which the intestine is generally partially sealed intermediate the two balloons.

It is appreciated that inflation of the intestine in the region between the two balloons may assist in realization of the operative orientations which are described hereinabove, corresponding to FIGS. 17A-17J, and in the overall propagation of endoscope 401 and endoscope tool 410 within the intestine.

Air flow may be provided to the intestinal volume between the two balloons through the instrument channel 460 of endoscope 401 as well known and commonly practiced in conventional endoscopy, or via the external tube 408, through the volume between the guiding tube 412 and external tube 408. Alternatively, endoscopy auxiliary assembly 402 may include more than one external tube 408 and in such a case air flow may be provided to the intestinal volume between the two balloons through an additional external tube (not shown).

It is appreciated that in any apparatus comprising two inflatable balloons which propagate relative to each other along a generally tubular body portion and specifically within an intestine, inflation of the generally tubular body portion and specifically the intestine intermediate the two balloons may assist in the propagation of the balloons.

It is appreciated that any other fluid may be supplied to the intestine intermediate the two balloons. For example, a liquid may be supplied intermediate the two balloons while the balloons are inflated and engaging the interior walls of the intestine, as seen in FIGS. 17D, 17E, 17H and 17I, thereby confining the liquid within the volume of the intestine intermediate the two balloons. Such a liquid may be a medicine or other treatment liquid, a rinsing solution, a marking agent, an ultrasound medium, or another suitable type of liquid.

It is appreciated that vacuum may be applied to the intestine intermediate the two balloons instead of a fluid, if applicable, such as for suctioning a previously inserted fluid, for assisting in the propagation of endoscope 401 or endoscope tool 410, or for cleaning body fluids during an endoscopy procedure.

Figure 18A:
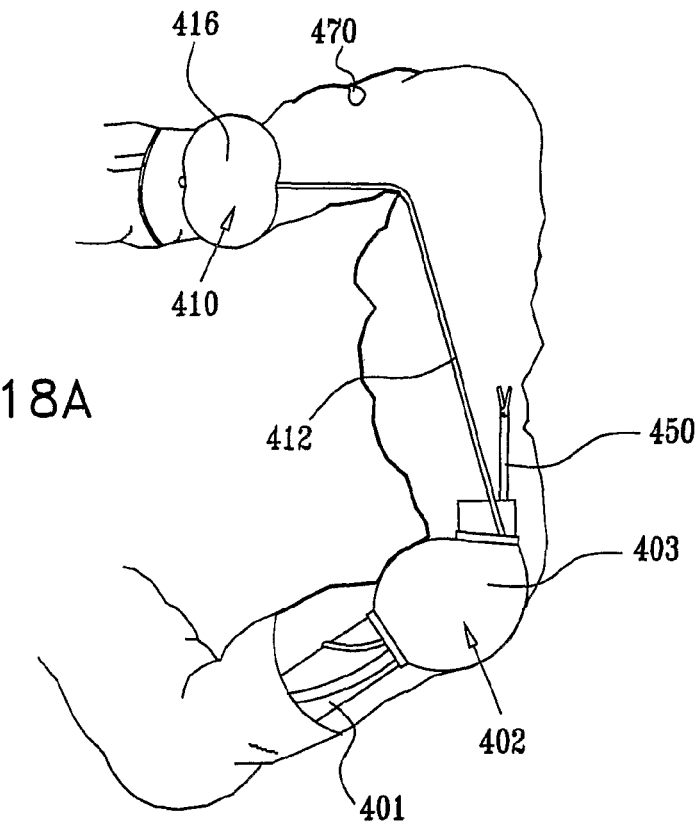
FIGS. 18A and 18B are simplified illustrations of a functionality which may be provided by the system of FIGS. 13-16B.
Figure 18B:
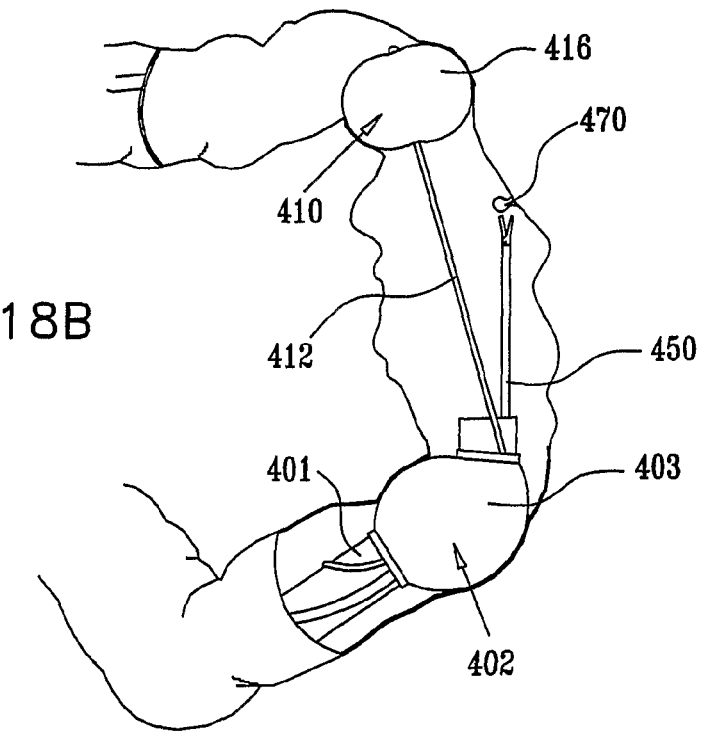

Reference is now made to FIGS. 18A and 18B, which are simplified illustrations of the embodiment of FIGS. 13-16B in a mode of operation useful for in-vivo inspection, diagnosis, sampling or treatment of a generally tubular body portion. As seen in FIG. 18A, peripheral balloon 403 is inflated and engaged with an interior wall of the generally tubular body portion, thereby anchoring the endoscope 401 thereat. Similarly, balloon 416 is inflated and engaged with an interior wall of the generally tubular body portion, thereby anchoring the endoscope tool 410 thereat.

FIG. 18A further shows a target location 470 at an interior wall of the generally tubular body portion, located intermediate peripheral balloon 403 and balloon 416. As seen in FIG. 18B, endoscope tool 410 may be pulled while still anchored to the interior wall of the generally tubular body portion by pulling guiding tube 412, thereby relocating the generally tubular body portion intermediate peripheral balloon 403 and balloon 416 towards the distal end of endoscope 401. This movement is operative to facilitate access of accessory 450 to target location 470, thereby enabling accessory 450 to perform medical interaction with target location 470, as applicable.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. An endoscope assembly for use with an endoscope and comprising:
a tubular sleeve circumferentially mountable onto a distal portion of said endoscope, said tubular sleeve having a circumferential wall in which is formed a tubular passageway, said tubular passageway comprising a plurality of non-interconnected mutually longitudinally spaced relatively rigid tubular reinforcement elements configured to permit predetermined bending of said tubular passageway and to facilitate passage of an endoscope tool therethrough within said tubular passageway and outwardly of said endoscope, said plurality of non-interconnected mutually longitudinally spaced relatively rigid tubular reinforcement elements each having a length which is greater than a longitudinal spacing therebetween;
a selectably inflatable balloon arranged to be mounted over said tubular sleeve; and
an external tube having a proximal end adapted to be located adjacent a proximal end of said endoscope and a distal end adapted to be located adjacent or forward of said distal portion of said endoscope, said external tube being adapted to extend outside of and alongside said endoscope from said proximal end thereof to said distal end thereof and to extend through said tubular passageway formed in said circumferential wall of said tubular sleeve, said external tube traversing said selectably inflatable balloon by passing between said selectably inflatable balloon and said distal portion of said endoscope.

2. An endoscope assembly according to claim 1 and also comprising an endoscope tool at least part of which is arranged to extend through said external tube, said endoscope tool including a selectably inflatable balloon.

3. An endoscope assembly according to claim 2 and wherein said endoscope tool is slidably insertable through said external tube.

4. An endoscope assembly according to claim 2 and wherein said endoscope tool is not insertable through said external tube.

5. An endoscope assembly according to claim 4 and wherein said endoscope tool is slidably insertable through said tubular passageway.

6. An endoscope assembly according to claim 2 and wherein said endoscope tool is bendable forwardly of said external tube.

7. An endoscope assembly according to claim 2 and also comprising a balloon inflation/deflation controller adapted to inflate at least said selectably inflatable balloon to a predetermined anchoring pressure within a generally tubular body portion, and wherein said at least said selectably inflatable balloon has an expansion diameter range which is larger than the maximum cross sectional diameter of said generally tubular body portion.

8. An endoscope assembly according to claim 1 and also comprising fluid supply functionality adapted for supplying a fluid via said external tube.

9. An endoscope assembly according to claim 1 and also comprising a balloon inflation/deflation controller adapted to inflate said selectably inflatable balloon to a predetermined anchoring pressure within a generally tubular body portion, and wherein said selectably inflatable balloon has an expansion diameter range which is larger than the maximum cross sectional diameter of said generally tubular body portion.

10. An endoscope assembly according to claim 9 and wherein said balloon inflation/deflection controller is also adapted to inflate said selectably inflatable balloon to a pressure of between 30 and 70 millibar, which is less than said predetermined anchoring pressure, and to an expansion diameter less than the maximum cross sectional diameter of said tubular body portion.

11. An endoscopy method comprising:
providing an endoscope having a distal portion;
circumferentially mounting a tubular sleeve, having a circumferential wall in which is formed a tubular passageway, onto said distal portion of said endoscope, said tubular passageway comprising a plurality of non-interconnected mutually longitudinally spaced relatively rigid tubular reinforcement elements configured to permit predetermined bending of said tubular passageway and to facilitate passage of an endoscope tool therethrough within said tubular passageway and outwardly of said endoscope, said plurality of non-interconnected mutually longitudinally spaced relatively rigid tubular reinforcement elements each having a length which is greater than a longitudinal spacing therebetween;

providing a selectably inflatable endoscope balloon having an external tube traversing said inflatable endoscope balloon, said external tube having a proximal end adapted to be located adjacent a proximal end of said endoscope and a distal end adapted to be located adjacent or forward of a distal end of said endoscope;

extending said external tube outside of and alongside said endoscope from said proximal end thereof to said distal end thereof and through said tubular passageway formed in said circumferential wall of said tubular sleeve, thereby traversing said selectably inflatable balloon by passing between said selectably inflatable balloon and said distal portion of said endoscope; and mounting onto said distal portion of said endoscope said selectably inflatable endoscope balloon having said external tube traversing said selectably inflatable endoscope balloon.

12. An endoscopy method according to claim 11 and wherein said mounting includes initially mounting said selectably inflatable endoscope balloon at said distal portion and thereafter mounting said external tube.

13. An endoscopy method according to claim 12 and wherein mounting said external tube includes placing said external tube between said selectably inflatable endoscope balloon and said distal portion of said endoscope.

14. An endoscopy method according to claim 11 and also comprising:

positioning a first endoscope tool having a selectably inflatable endoscope tool balloon forwardly of said selectably inflatable endoscope balloon.

15. An endoscopy method according to claim 14 and also comprising:

positioning a second endoscope tool rearwardly of said first selectably inflatable endoscope tool balloon and forwardly of said selectably inflatable endoscope balloon.

* * * * *